(12) United States Patent
Vandyck et al.

(10) Patent No.: US 9,567,299 B2
(45) Date of Patent: Feb. 14, 2017

(54) CARBOXAMIDE DERIVATIVES AND THE USE THEREOF AS MEDICAMENTS FOR THE TREATMENT OF HEPATITIS B

(71) Applicant: Janssen Sciences Ireland UC, Co Cork (IE)

(72) Inventors: Koen Vandyck, Paal-Beringen (BE); Geerwin Yvonne Paul Haché, Kapellen (BE); Bart Rudolf Romanie Kesteleyn, Berlare (BE); Pierre Jean-Marie Bernard Raboisson, Rosieres (BE)

(73) Assignee: JANSSEN SCIENCES IRELAND UC, Little Island, Co Cork (IE)

( * ) Notice: Subject to any disclaimer, the term of this patent is extended or adjusted under 35 U.S.C. 154(b) by 0 days.

(21) Appl. No.: 15/031,493

(22) PCT Filed: Oct. 22, 2014

(86) PCT No.: PCT/EP2014/072690
§ 371 (c)(1),
(2) Date: Apr. 22, 2016

(87) PCT Pub. No.: WO2015/059212
PCT Pub. Date: Apr. 30, 2015

(65) Prior Publication Data
US 2016/0264522 A1     Sep. 15, 2016

(30) Foreign Application Priority Data

Oct. 23, 2013  (EP) .................................... 13189880

(51) Int. Cl.
| C07D 207/18 | (2006.01) |
| A61K 31/40 | (2006.01) |
| C07D 207/09 | (2006.01) |
| C07D 405/12 | (2006.01) |
| C07D 207/16 | (2006.01) |
| C07D 211/60 | (2006.01) |
| A61K 31/445 | (2006.01) |
| A61K 45/06 | (2006.01) |
| C07D 211/34 | (2006.01) |

(52) U.S. Cl.
CPC ............ *C07D 207/09* (2013.01); *A61K 31/40* (2013.01); *A61K 31/445* (2013.01); *A61K 45/06* (2013.01); *C07D 207/16* (2013.01); *C07D 211/34* (2013.01); *C07D 211/60* (2013.01); *C07D 405/12* (2013.01)

(58) Field of Classification Search
CPC .............................. C07D 207/08; A61K 31/40
USPC ................... 548/538; 546/226; 514/330, 423
See application file for complete search history.

(56) References Cited

U.S. PATENT DOCUMENTS

| 2003/0114443 A1 | 6/2003 | Imamura et al. |
| 2016/0051512 A1* | 2/2016 | Vandyck .............. C07D 209/52 514/409 |

FOREIGN PATENT DOCUMENTS

WO     WO2013/006394 A1     1/2013

OTHER PUBLICATIONS

Geng et al, Mini-Reviews in Medicinal Chemistry vol. 13 pp. 749-776 XP055105561; XP009176654 , 2013.
Qiu et al, Fundamental & Clinical Pharmacology; XP055105340 , 2013.
International Search Report and Written Opinion dated Jan. 8, 2015, for International Application No. PCT/EP2013/072690.
European Extended Search Report dated Mar. 28, 2014, for European Application No. EP13189880.1.

* cited by examiner

*Primary Examiner* — Charanjit Aulakh

(57) ABSTRACT

Inhibitors of HBV replication of formula (I)

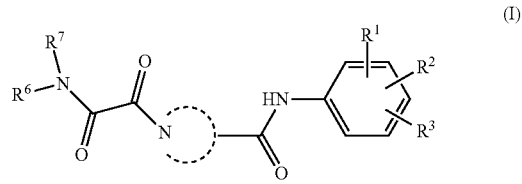

including stereochemically isomeric forms, and salts, hydrates, solvates thereof, wherein X, $R^1$ to $R^7$ have the meaning as defined herein.
The present invention also relates to processes for preparing said compounds, pharmaceutical compositions containing them and their use, alone or in combination with other HBV inhibitors, in HBV therapy.

19 Claims, No Drawings

CARBOXAMIDE DERIVATIVES AND THE USE THEREOF AS MEDICAMENTS FOR THE TREATMENT OF HEPATITIS B

CROSS-REFERENCE TO RELATED APPLICATIONS

This application is the national stage filing under USC 371 of international application PCT/EP2014/072690 filed on Oct. 22, 2014, which claims priority to European Patent Application No. 13189880.1 filed Oct. 23, 2013, the complete disclosures of which are hereby incorporated herein by reference for all purposes.

BACKGROUND ART

The Hepatitis B virus (HBV) is an enveloped, partially double-stranded DNA (dsDNA) virus of the Hepadnavirus family (Hepadnaviridae). Its genome contains 4 overlapping reading frames: the precore/core gene; the polymerase gene; the L, M, and S genes, which encode for the 3 envelope proteins; and the X gene.

Upon infection, the partially double-stranded DNA genome (the relaxed circular DNA; rcDNA) is converted to a covalently closed circular DNA (cccDNA) in the nucleus of the host cell and the viral mRNAs are transcribed. Once encapsidated, the pregenomic RNA (pgRNA), which also codes for core protein and Pol, serves as the template for reverse transcription, which regenerates the partially dsDNA genome (rcDNA) in the nucleocapsid.

HBV has caused epidemics in parts of Asia and Africa, and it is endemic in China. HBV has infected approximately 2 billion people worldwide of which approximately 350 million people have developed chronic infections. The virus causes the disease hepatitis B and chronic infection is correlated with a strongly increased risk for the development cirrhosis and hepatocellular carcinoma.

Transmission of hepatitis B virus results from exposure to infectious blood or body fluids, while viral DNA has been detected in the saliva, tears, and urine of chronic carriers with high titer DNA in serum.

An effective and well-tolerated vaccine exists, but direct treatment options are currently limited to interferon and the following antivirals; tenofovir, lamivudine, adefovir, entecavir and telbivudine.

In addition, heteroaryldihydropyrimidines (HAPs) were identified as a class of HBV inhibitors in tissue culture and animal models (Weber et al., Antiviral Res. 54: 69-78).

WO2013/006394, published on Jan. 10, 2013, relates to Sulphamoyl-arylamides active against HBV.

WO/2013/096744, published on Jun. 26, 2013 relates to compounds active against HBV.

Amongst the problems which HBV direct antivirals may encounter are toxicity, mutagenicity, lack of selectivity, poor efficacy, poor bioavailability, and difficulty of synthesis.

There is a need for additional HBV inhibitors that may overcome at least one of these disadvantages or that have additional advantages such as increased potency or an increased safety window.

DESCRIPTION OF THE INVENTION

The present invention relates to a compound of Formula (I)

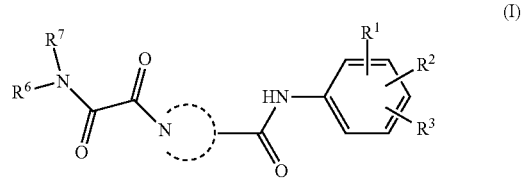

or a stereoisomer or tautomeric form thereof, wherein:

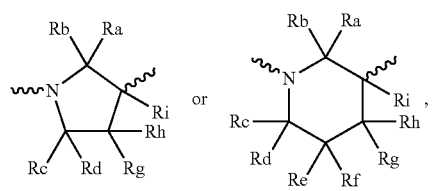

represents

each of Ra, Rb, Rc, Rd, Re, Rf and Rg are independently selected from the group consisting of Hydrogen and methyl;
Rh is Hydrogen;
Ri is Hydrogen;
$R^1$, $R^2$ and $R^3$ are independently selected from the group consisting of Hydrogen, Fluoro, Chloro, Bromo, —$CHF_2$, —$CH_2F$, —$CF_3$, —CN and methyl;
$R^6$ is selected from the group consisting of $C_1$-$C_6$alkyl and a 3-7 membered saturated ring optionally containing one or more heteroatoms each independently selected from the group consisting of O, S and N, such $C_1$-$C_6$alkyl or 3-7 membered saturated ring optionally substituted with one or more substituents selected from the group consisting of Fluoro, $C_1$-$C_3$alkyl optionally substituted with one or more Fluoro, —CN, OH;
$R^7$ represents hydrogen;
or a pharmaceutically acceptable salt or a solvate thereof.

The invention further relates to a pharmaceutical composition comprising a compound of Formula (I), and a pharmaceutically acceptable carrier.

The invention also relates to the compounds of formula (I) for use as a medicament, preferably for use in the prevention or treatment of an HBV infection in a mammal.

In a further aspect, the invention relates to a combination of a compound of formula (I), and another HBV inhibitor.

DEFINITIONS

The term "$C_{1-3}$alkyl" or $C_1$-$C_4$alkyl as a group or part of a group refers to a hydrocarbyl radical of Formula $C_nH_{2n+1}$ wherein n is a number ranging from 1 to 3. In case $C_{1-3}$alkyl is coupled to a further radical, it refers to a Formula $CH_{2n}$. $C_{1-3}$alkyl groups comprise from 1 to 3 carbon atoms, more preferably 1 to 2 carbon atoms. $C_{1-3}$alkyl includes all linear, or branched alkyl groups with between 1 and 3 carbon atoms, and thus includes such as for example methyl, ethyl, n-propyl, and i-propyl.

$C_{1-4}$alkyl as a group or part of a group defines straight or branched chain saturated hydrocarbon radicals having from 1 to 4 carbon atoms such as the group defined for $C_{1-3}$alkyl and butyl and the like.

$C_{1-6}$alkyl, $C_{2-6}$alkyl and $C_{3-6}$alkyl as a group or part of a group defines straight or branched chain saturated hydrocarbon radicals having from 1 to 6 carbon atoms, or from 2 to 6 carbon atoms or from 3 to 6 carbon atoms such as the groups defined for $C_{1-4}$alkyl and pentyl, hexyl, 2-methylbutyl and the like.

As used herein, the term "3-7 membered saturated ring" means saturated cyclic hydrocarbon with 3, 4, 5, 6 or 7 carbon atoms and is generic to cyclopropyl, cyclobutyl, cyclopentyl, cyclohexyl and cycloheptyl or $C_3$-, $C_4$-, $C_5$-, $C_6$- or $C_7$-cycloalkyl.

Such saturated ring optionally contains one or more heteroatoms, such that at least one carbon atom is replaced by a heteroatom selected from N, O and S, in particular from N and O. Examples include oxetane, tetrahydro-2H-pyranyl, piperidinyl, tetrahydrofuranyl, morpholinyl, thiolane 1,1-dioxide and pyrrolidinyl. Preferred are saturated cyclic hydrocarbon with 3 or 4 carbon atoms and 1 oxygen atom. Examples include oxetane, and tetrahydrofuranyl.

The term halo and halogen are generic to Fluoro, Chloro, Bromo or Iodo. Preferred halogens are Fluoro and Chloro.

It should also be noted that the radical positions on any molecular moiety used in the definitions may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

A bond indicated with

indicates the attachment of the indicated fragment to the main structure of the molecule.

Positions indicated on phenyl (e.g. ortho, meta and/or para) are indicated relative to the bond connecting the phenyl to the main structure. An example with regard to the position of any location is indicated relative to the nitrogen (*) connected to the main structure:

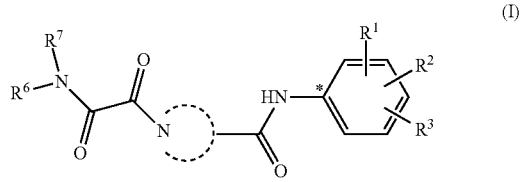

(I)

When any variable (e.g. halogen or $C_{1-4}$alkyl) occurs more than one time in any constituent, each definition is independent.

For therapeutic use, the salts of the compounds of formula (I) are those wherein the counter ion is pharmaceutically or physiologically acceptable. However, salts having a pharmaceutically unacceptable counter ion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The term "salts" also comprises the hydrates and the solvent addition forms that the compounds of the present invention are able to form. Examples of such forms are e.g. hydrates, alcoholates and the like.

The present compounds may also exist in their tautomeric forms. For example, tautomeric forms of amide (—C(=O)—NH—) groups are iminoalcohols (—C(OH)=N—). Tautomeric forms, although not explicitly indicated in the structural formulae represented herein, are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric forms of formula (I) can be obtained separately by conventional methods. Appropriate physical separation methods that may advantageously be employed are, for example, selective crystallization and chromatography, e.g. column chromatography.

The present invention is also intended to include all isotopes of atoms occurring on the present compounds. Isotopes include those atoms having the same atomic number but different mass numbers. By way of general example and without limitation, isotopes of Hydrogen include tritium and deuterium. Isotopes of carbon include C-13 and C-14.

DETAILED DESCRIPTION OF THE INVENTION

Whenever used hereinafter, the term "compounds of formula (I)",

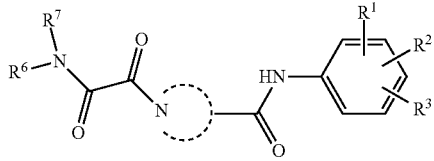

or, "the present compounds" or similar term is meant to include the compounds of general formula (I), (II), (III) salts, stereoisomeric forms and racemic mixtures or any subgroups thereof.

In a first aspect, the invention provides compound of Formula (I)

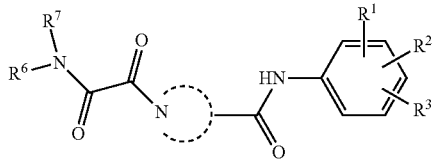

or a stereoisomer or tautomeric form thereof, wherein:

represents

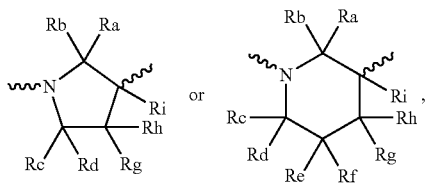

each of Ra, Rb, Rc, Rd, Re, Rf and Rg are independently selected from the group consisting of Hydrogen and methyl;
Rh is Hydrogen;
Ri is Hydrogen;
$R^1$, $R^2$ and $R^3$ are independently selected from the group consisting of Hydrogen, Fluoro, Chloro, Bromo, —$CHF_2$, —$CH_2F$, —$CF_3$, —CN and methyl;
$R^6$ is selected from the group consisting of $C_1$-$C_6$alkyl and a 3-7 membered saturated ring optionally containing one or more heteroatoms each independently selected from the group consisting of O, S and N, such $C_1$-$C_6$alkyl or 3-7 membered saturated ring optionally substituted with one or more substituents selected from the group consisting of Fluoro, $C_1$-$C_3$alkyl optionally substituted with one or more Fluoro, —CN, OH;
$R^7$ represents hydrogen;
or a pharmaceutically acceptable salt or a solvate thereof.

In a second aspect, the invention provides compound of Formula (II)

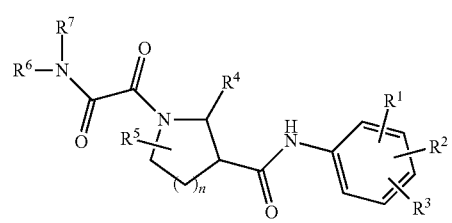

or Formula (III)

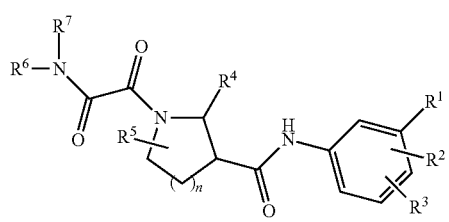

or a stereoisomer or tautomeric form thereof, wherein:
n indicates an integer of 1 or 2;
$R^1$, $R^2$ and $R^3$ are independently selected from the group consisting of Hydrogen, Fluoro, Chloro, Bromo, —$CHF_2$, —$CH_2F$, —$CF_3$, —CN and methyl;
$R^4$ and $R^5$ are independently selected from Hydrogen or methyl;
$R^6$ is selected from the group consisting of $C_1$-$C_6$alkyl and a 3-7 membered saturated ring optionally containing one or more heteroatoms each independently selected from the group consisting of O, S and N, such $C_1$-$C_6$alkyl or 3-7 membered saturated ring optionally substituted with one or more substituents selected from the group consisting of Fluoro, $C_1$-$C_3$alkyl optionally substituted with one or more Fluoro, —CN, OH;

$R^7$ represents hydrogen;

or a pharmaceutically acceptable salt or a solvate thereof.

In a first embodiment, compounds of Formula (I), (II) or (III) are provided wherein $R^6$ is selected from the group consisting of $C_1$-$C_6$alkyl and a 3-7 membered saturated ring optionally containing one or more heteroatoms each independently selected from the group consisting of O, S and N, such $C_1$-$C_6$alkyl or 3-7 membered saturated ring optionally substituted with one or more substituents selected from the group consisting of Fluoro, $C_1$-$C_3$alkyl, —CN, OH.

In one embodiment, compounds of the present invention are provided wherein $R^1$ is selected from hydrogen, Fluoro, Chloro, —CHF$_2$, —CN, —CF$_3$ or methyl. In a further embodiment, least two of $R^1$, $R^2$ and $R^3$ are Fluoro, Chloro or Bromo. In a further embodiment, 1e is not Hydrogen.

In another embodiment, $R^4$ is methyl.

In yet another embodiment, compounds according to the invention are indicated wherein $R^6$ contains a 3-7 membered saturated ring optionally containing one oxygen, such 3-7 membered saturated ring optionally substituted with methyl. Preferably, $R^6$ is a 4 or 5 membered saturated ring containing one oxygen, such 4 or 5 membered saturated ring optionally substituted with methyl.

In another embodiment, $R^6$ is a branched $C_1$-$C_6$alkyl optionally substituted with one or more Fluoro.

Preferred compounds according to the invention are provided wherein the stereochemical configuration of atom (*) is as follows

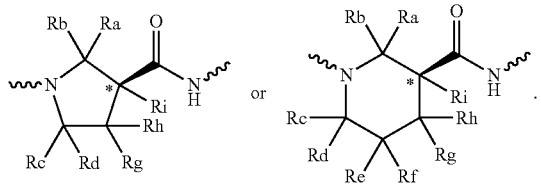

Another embodiment of the present invention relates to those compounds of Formula (I), (II) or (III) or any subgroup thereof as mentioned in any of the other embodiments wherein one or more of the following restrictions apply:

(a)

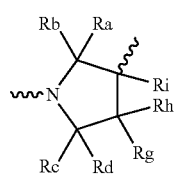

represents

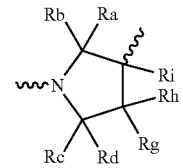

and $R^6$ is selected from the group consisting of $C_1$-$C_6$alkyl optionally being substituted with one or more Fluoro;

(a)

represents and $R^2$ is Hydrogen or Fluoro.

(c) $R^1$ and $R^3$ are independently selected from the group consisting of Hydrogen, Fluoro, Chloro —CN and methyl.

(d) $R^2$ is Hydrogen or Fluoro and $R^1$ and $R^3$ are independently selected from the group consisting of Hydrogen, Fluoro, Chloro and CN.

(e) $R^6$ comprises a branched $C_3$-$C_6$alkyl optionally substituted with one or more Fluoro, or wherein $R^6$ comprises a $C_3$-$C_6$cycloalkyl wherein such $C_3$-$C_6$cycloalkyl is substituted with $C_1$-$C_3$alkyl substituted with one or more Fluoro.

Further combinations of any of the embodiments are also in the scope of the present invention.

Preferred compounds according to the invention are compounds 1-35 or a stereoisomer or tautomeric form thereof as referenced to in Table 1.

In a further aspect, the present invention concerns a pharmaceutical composition comprising a therapeutically or prophylactically effective amount of a compound of formula (I) as specified herein, and a pharmaceutically acceptable carrier. A prophylactically effective amount in this context is an amount sufficient to prevent HBV infection in subjects being at risk of being infected. A therapeutically effective amount in this context is an amount sufficient to stabilize HBV infection, to reduce HBV infection, or to eradicate HBV infection, in infected subjects. In still a further aspect, this invention relates to a process of preparing a pharmaceutical composition as specified herein, which comprises intimately mixing a pharmaceutically acceptable carrier with a therapeutically or prophylactically effective amount of a compound of formula (I), as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) are active as inhibitors of the HBV replication cycle and can be used in the treatment and prophylaxis of HBV infection or diseases associated with HBV. The latter include progressive liver fibrosis, inflammation and necrosis leading to cirrhosis, end-stage liver disease, and hepatocellular carcinoma.

Due to their antiviral properties, particularly their anti-HBV properties, the compounds of formula (I) or any subgroup thereof, are useful in the inhibition of the HBV replication cycle, in particular in the treatment of warm-blooded animals, in particular humans, infected with HBV, and for the prophylaxis of HBV infections. The present invention furthermore relates to a method of treating a warm-blooded animal, in particular human, infected by HBV, or being at risk of infection by HBV, said method comprising the administration of a therapeutically effective amount of a compound of formula (I).

The compounds of formula (I), as specified herein, may therefore be used as a medicine, in particular as medicine to treat or prevent HBV infection. Said use as a medicine or method of treatment comprises the systemic administration to HBV infected subjects or to subjects susceptible to HBV infection of an amount effective to combat the conditions associated with HBV infection or an amount effective to prevent HBV infection.

The present invention also relates to the use of the present compounds in the manufacture of a medicament for the treatment or the prevention of HBV infection.

In general it is contemplated that an antiviral effective daily amount would be from about 0.01 to about 50 mg/kg, or about 0.01 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

The present invention also concerns combinations of a compound of formula (I) or any subgroup thereof, as specified herein with other anti-HBV agents. The term "combination" may relate to a product or kit containing (a) a compound of formula (I), as specified above, and (b) at least one other compound capable of treating HBV infection (herein designated as anti-HBV agent), as a combined preparation for simultaneous, separate or sequential use in treatment of HBV infections. In an embodiment, the invention concerns combination of a compound of formula (I) or any subgroup thereof with at least one anti-HBV agent. In a particular embodiment, the invention concerns combination of a compound of formula (I) or any subgroup thereof with at least two anti-HBV agents. In a particular embodiment, the invention concerns combination of a compound of formula (I) or any subgroup thereof with at least three anti-HBV agents. In a particular embodiment, the invention concerns combination of a compound of formula (I) or any subgroup thereof with at least four anti-HBV agents.

The term anti-HBV agent also includes compounds capable of treating HBV infection via immunomodulation. Examples of immunomodulators are interferon-α (IFN-α), pegylated interferon-α or stimulants of the innate immune system such as Toll-like receptor 7 and/or 8 agonists. One embodiment of the present invention relates to combinations of a compound of Formula (IA) or any subgroup thereof, as specified herein with an immunomodulating compound, more specifically a Toll-like receptor 7 and/or 8 agonist.

The combination of previously known anti-HBV agents, such as interferon-α (IFN-α), pegylated interferon-α, 3TC, adefovir or a combination thereof, and, a compound of formula (I) or any subgroup thereof can be used as a medicine in a combination therapy.

Generic Synthesis

The substituents represented by $R^{1,2,3}$, $R^7$ or $R^6$ in this general synthesis section are meant to include any substituent or reactive species that is suitable for transformation into any $R^{1,2,3}$ or $R^6$ substituent according to the present invention without undue burden for the person skilled in the art.

A possible synthesis of compounds of general formula (I) is described in scheme 1. A N-protected (where Pg is protecting group) aminocarboxylic acid of general formula (IV) can be selectively reacted with an aniline of general formula (V), for example by addition of aniline (V) to a mixture of compound (IV), and a coupling agent (e.g. HATU) in an aprotic solvent (e.g. dichloromethane, DMF), along with an organic base (e.g. triethylamine) resulting in compound (VI). The protecting group (Pg) can subsequently be deprotected according to known methods (e.g. For the boc group, deprotection involves addition of a strong acid like HCl. Benzyl protecting groups are removed via catalytic hydrogenation via known methods by one skilled in the art.) forming the amine salt which after solvent removal and addition of base (e.g. diisopropylethylamine) can be further reacted in one pot with ethyl chlorooxoacetate at reduced temperature in an aprotic solvent (e.g. dichloromethane) to afford compounds of type (VIII). The ester group of (VIII) is then hydrolyzed by known methods (e.g. addition of an aqueous base). In one pot, the newly formed acid is generated after decreasing the pH and removal of the solvent under reduced pressure. The acid functional group is converted to an amide functional group by use of a coupling agent (e.g. HATU) in an aprotic solvent (e.g. dichloromethane, DMF), along with an organic base (e.g. triethylamine), and amines (IX) resulting in compounds of formula (I). Alternatively, the ester functionality in compounds (VIII) can be converted to an amide via reaction with an amine (IX) in a closed vessel, or optionally in the presence of lithium bis(trimethylsilyl)amide at 0° C. in a solvent like THF.

formula XIV, which can be coupled with an amine of general formula V, for example under influence of a coupling agent (e.g. HATU) in an aprotic solvent (e.g. dichloromethane, DMF), along with an organic base (e.g. triethylamine), resulting in the formation of a compound of general formula I

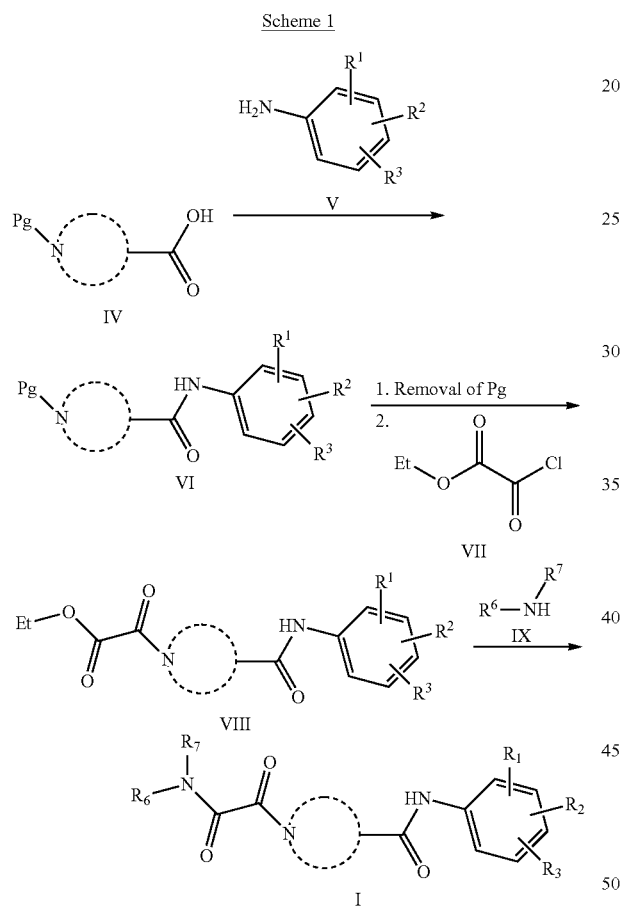

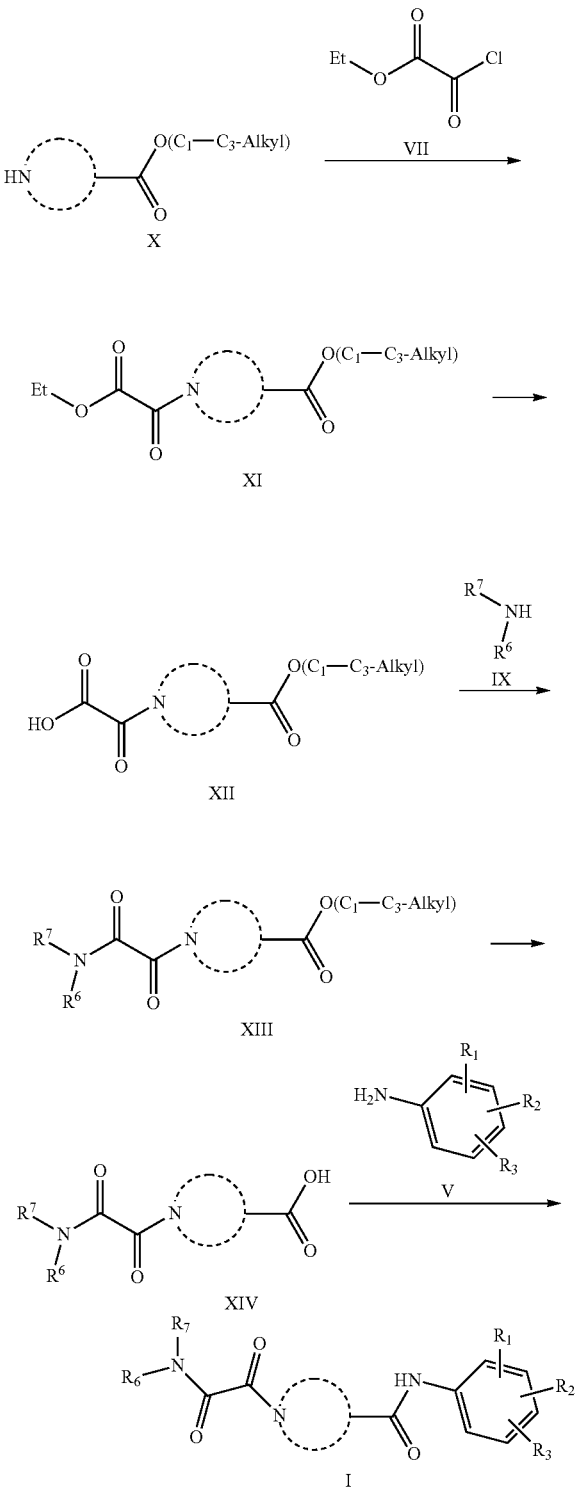

Scheme 2 describes another possible synthesis of a compound of general formula I. A compound of general formula X is reacted with ethyl chlorooxoacetate, resulting in a compound of general formula XI. After selective hydrolysis, for example in the presence of a base like NaOH at 0° C. in MeOH, compound XII is formed. This compound can be coupled with an amine of general formula IX in the presence of a coupling agent (e.g. HATU) in an aprotic solvent (e.g. dichloromethane, DMF), along with an organic base (e.g. triethylamine). Alternatively, compound XI can be directly converted into a compound of general formula XIII by reaction with an amine IX (for example in case of IX equals isopropylamine, in EtOH at 60° C.) resulting in the selective formation of a compound of formula XIII Hydrolysis of the ester functionality of XIII, result in a compound of general

Scheme 3

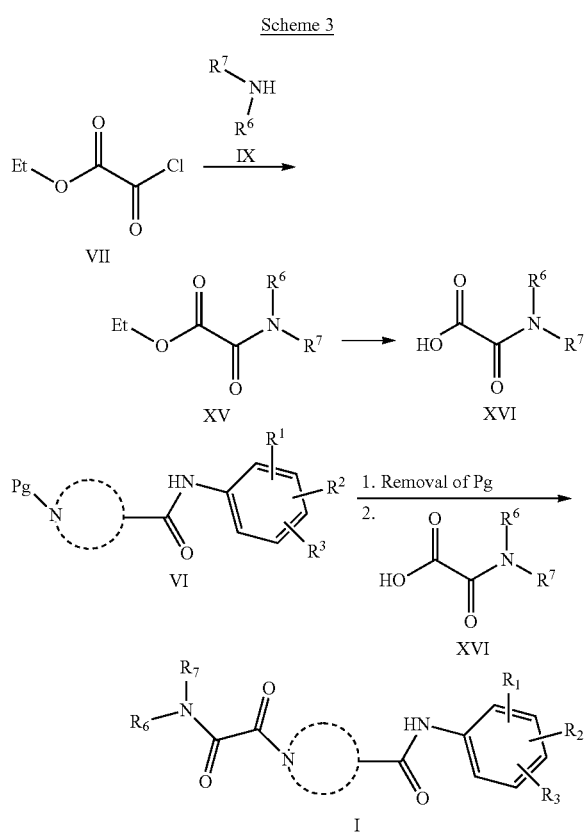

A reagent of general formula XVI, can be formed starting from reacting ethyl chlorooxoacetate with an amine of general formula IX, followed by ester hydrolysis, as shown in scheme 3. This reagent XVI, can be coupled with an amine, for example obtained after deprotection of VI, in the presence of coupling agent (e.g. HATU) in an aprotic solvent (e.g. dichloromethane, DMF), along with an organic base (e.g. triethylamine), resulting in a compound of general formula I.

General Procedure LCMS Methods

The High Performance Liquid Chromatography (HPLC) measurement was performed using a LC pump, a diode-array (DAD) or a UV detector and a column as specified in the respective methods. If necessary, additional detectors were included (see table of methods below). Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc.). All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica, "Q-Tof" Quadrupole Time-of-flight mass spectrometers, "CLND", ChemiLuminescent Nitrogen Detector, "ELSD" Evaporative Light Scanning Detector, LCMS Methods (Flow expressed in mL/min; column temperature (T) in ° C.; Run time in minutes). The instrument used was a Waters: Acquity® UPLC®-DAD and SQD.

| Method code | Column | Mobile phase | Gradient | Flow / Col T | Run time |
|---|---|---|---|---|---|
| A | Waters: BEH C18 (1.7 µm, 2.1 × 50 mm) | A: 0.1% HCOOH + 5% CH$_3$OH in H$_2$O B: CH$_3$CN | From 95% A to 0% A in 2.5 min, to 5% A in 0.5 min. | 0.8 / 55 | 3 |
| B | Waters: BEH C18 (1.7 µm, 2.1 × 50 mm) | A: 10 mM CH$_3$COONH$_4$ in 95% H$_2$O + 5% CH$_3$CN B: CH$_3$CN | From 95% A to 5% A in 1.3 min, held for 0.7 min. | 0.8 / 55 | 2 |
| C | Waters: HSS T3 (1.8 µm, 2.1 × 100 mm) | A: 10 mM CH$_3$COONH$_4$ in 95% H$_2$O + 5% CH$_3$CN B: CH$_3$CN | From 100% A to 5% A in 2.10 min, to 0% A in 0.90 min, to 5% A in 0.5 min | 0.8 / 55 | 3.5 |
| D | Waters: HSS T3 (1.8 µm, 2.1*100 mm) | A: 10 mM CH$_3$COONH$_4$ in 95% H$_2$O + 5% CH$_3$CN B: CH3CN | From 100% A to 5% A in 2.10 min, to 0% A in 0.90 min, to 5% A in 0.5 min | 0.7 / 55 | 3.5 |

Synthesis of Compounds

Compound 1: (S)—N-(3-bromo-4,5-difluorophenyl)-1-(2-oxo-2-(((R)-1,1,1-trifluoropropan-2-yl)amino)acetyl)pyrrolidine-3-carboxamide

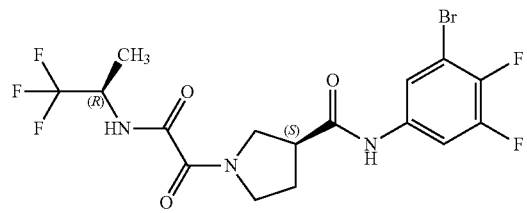

Step 1. Synthesis of (S)—N-(3-bromo-4,5-difluoro-phenyl)pyrrolidine-3-carboxamide N-Boc-(3S)-1-pyrrolidine-3-carboxylic acid [CAS 140148-70-5] (1 g, 4.65 mmol), 3-bromo-4,5-difluoroaniline (0.96 g, 4.65 mmol) and HATU (2.12 g, 5.58 mmol) were added to CH$_2$Cl$_2$ (10 mL). N,N-diisopropylethylamine (2.4 mL, 13.9 mmol) was added and the resultant mixture stirred at room temperature for 4 hours. The mixture was partitioned with HCl (1M, aq., 20 mL). The organic layer was separated and the solvent removed under reduced pressure. The crude was purified via silica gel column chromatography using a heptane to ethyl acetate gradient to afford an oil. Subsequent Boc deprotection HCl (6 M in isopropanol, 15 h at room temperature) afforded (S)—N-(3-bromo-4,5-difluorophenyl)pyrrolidine-3-carboxamide hydrochloride that was used as such in the next step without further purification.

Step 2. Synthesis of (S)-ethyl 2-(3-((3-bromo-4,5-difluorophenyl)carbamoyl) pyrrolidin-1-yl)-2-oxoacetate A mixture of (S)—N-(3-bromo-4,5-difluorophenyl) pyrrolidine-3-carboxamide hydrochloride (1.8 g), and triethylamine (1.47 mL, 10.54 mmol) in $CH_2Cl_2$ (20 mL) was cooled to 0° C. To this mixture was added ethyl chloro oxoacetate (0.65 mL, 5.8 mmol) dropwise, and the reaction mixture was stirred for one hour at 0° C., followed by the addition of ethyl acetate (100 mL). The organic layer was washed (1M HCl aq., $NaHCO_3$ aq., and brine), dried over magnesium sulfate, the solids were removed by filtration and the solvent of the filtrate was removed under reduced pressure. The crude intermediate was used as such without further purification in the next step.

Step 3

(S)-2-(3-((3-bromo-4,5-difluorophenyl)carbamoyl)pyrrolidin-1-yl)-2-oxoacetic acid was afforded after the corresponding ethyl ester was hydrolyzed using sodium hydroxide in ethanol for 15 minutes at room temperature. The reaction mixture was cooled to 0° C. HCl (1M aq.) was added to bring the mixture to approximately pH 2. Brine (30 mL) was added and the mixture was partitioned with ethyl acetate (3×50 mL). The organic layers were pooled, washed with brine (20 mL), dried over sodium sulfate, the solids were removed by filtration, and the solvent was removed under reduced pressure to afford the title compound as an oil. No further purification was done.

Step 4. Preparation of (S)—N-(3-bromo-4,5-difluorophenyl)-1-(2-oxo-2-(((R)-1,1,1-trifluoropropan-2-yl)amino)acetyl)pyrrolidine-3-carboxamide A mixture of (S)-2-(3-((3-bromo-4,5-difluorophenyl)carbamoyl)pyrrolidin-1-yl)-2-oxoacetic acid (450 mg), HATU (0.499 g, 1.31 mmol), diisopropylethylamine (463 mg, 3.58 mmol), (R)-1,1,1-trifluoro-2-propylamine (135 mg, 1.19 mmol), and DMF (8 mL) were allowed to stir at room temperature for 2 hours. To the reaction mixture was added ethyl acetate (100 mL). The organic layer was washed with 1M HCl (aq.), sodium bicarbonate (sat., aq.), and brine. The solvents were removed under reduced pressure and the crude was purified by reverse phase preperative HPLC (stationary phase: RP Vydac Denali C18-10 µm, 200 g, 5 cm), mobile phase: 0.25% $NH_4HCO_3$ solution in water, $CH_3CN$). The desired fractions were pooled and the solvent was removed under reduced pressure to afford compound 1 as a white solid. Method A, Rt=1.63 min, m/z=470.0 (M–H)⁻, exact mass: 471.0, ¹H NMR (400 MHz, DMSO-$d_6$) δ ppm 1.30 (d, J=7.0 Hz, 3H), 1.97-2.31 (m, 2H), 3.10-3.27 (m, 1H), 3.39-3.96 (m, 4H), 4.51-4.75 (m, 1H), 7.57-7.80 (m, 2H), 9.26 (br. s., 1H), 10.41 (br. s., 1H)

Compound 2: (S)—N-(3-bromo-4,5-difluorophenyl)-1-(2-((3-methyloxetan-3-yl)amino)-2-oxoacetyl)pyrrolidine-3-carboxamide

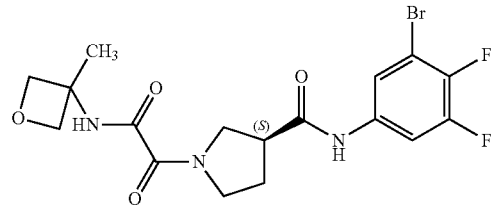

Compound 2 was made according to the method described for compound 1 with the exception that, in step 4, 3-methyloxetan-3-amine was employed instead of (R)-1,1,1-trifluoro-2-propylamine. Method A, Rt=1.44 min, m/z=444.0 (M–H)⁻, exact mass: 445.0. ¹H NMR (400 MHz, DMSO-$d_6$) δ ppm 1.46-1.57 (m, 6H), 1.92-2.32 (m, 4H), 3.08-3.24 (m, 2H), 3.43 (dt, J=12.3, 7.5 Hz, 1H), 3.49-3.61 (m, 2H), 3.62-3.77 (m, 2H), 3.78-3.90 (m, 2H), 3.99 (dd, J=11.8, 7.6 Hz, 1H), 4.25-4.37 (m, 4H), 4.58-4.70 (m, 4H), 7.55-7.86 (m, 4H), 9.18 (br. s., 2H), 10.40 (br. s., 2H), as a mixture of rotamers.

Compound 3: (S)—N-(3-bromo-4,5-difluorophenyl)-1-(2-(tert-butylamino)-2-oxoacetyl)-pyrrolidine-3-carboxamide

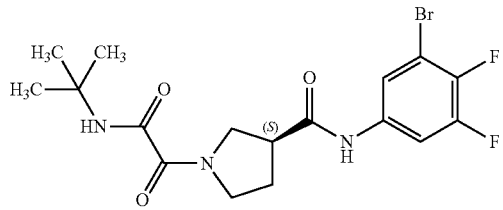

Compound 3 was made according to the method described for compound 1 with the exception that, in step four, 2-methylpropan-2-amine was employed instead of (R)-1,1,1-trifluoro-2-propylamine. Method A, Rt=1.63 min, m/z=430.0 (M–H)⁻, Exact mass: 431.1. ¹H NMR (400 MHz, DMSO-$d_6$) δ ppm 1.24-1.36 (m, 9H), 1.91-2.29 (m, 2H), 3.06-3.25 (m, 1H), 3.37-4.01 (m, 4H), 7.60-7.80 (m, 2H), 7.96-8.03 (m, 1H), 10.39 (br. s., 1H).

Compound 4: (3S)—N-(4-Fluoro-3-methylphenyl)-1-{[(1-methylethyl)amino](oxo)acetyl}-pyrrolidine-3-carboxamide

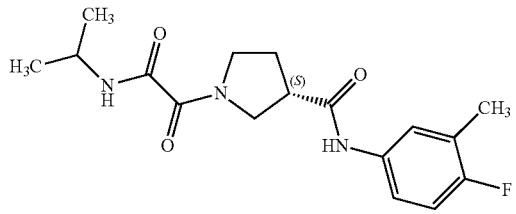

Step 1. Preparation of (S)-tert-butyl 3-((4-fluoro-3-methylphenyl)carbamoyl) pyrrolidine-1-carboxylate N-Boc-(3S)-1-pyrrolidine-3-carboxylic acid CAS [140148-70-5] (20 g, 92.9 mmol), 4-fluoro-3-methylaniline (11.63 g, 92.9 mmol), and N, N-diisopropylethylamine (48 mL, 279 mmol) were added to $CH_2Cl_2$ (300 mL) at room temperature. HATU (42.4 g, 111.5 mmol) was added in small portions and the resultant mixture stirred at room temperature for 15 hours. The mixture was partitioned with HCl (1 M, aq., 20 mL). The organic layer was separated and the solvent removed under reduced pressure. The crude was purified via silica gel column chromatography using a heptane to ethyl acetate gradient to afford an oil. Subsequent Boc-deprotection HCl (6 M in isopropanol, 15 hours at room temperature) afforded (S)—N-(4-fluoro-3-methylphenyl) pyrrolidine-3-carboxamide hydrochloride that was used as such in the next step without further purification.

Step 2. Preparation of (9-ethyl 2-(3-((4-fluoro-3-methylphenyl)carbamoyl)pyrrolidin-1-yl)-2-oxoacetate A mixture of (S)—N-(4-fluoro-3-methylphenyl)pyrrolidine-3-carboxamide hydrochloride (0.5 g), and triethylamine (587 mg, 5.80 mmol) in $CH_2Cl_2$ (10 mL) was cooled to 0° C. To this mixture was added ethyl chlorooxoacetate (290 mg, 2.13 mmol) dropwise, and the reaction mixture stirred for one hour and 20 minutes at 0° C., followed by the addition of ethyl acetate. The organic layer was washed (1 M HCl aq., $NaHCO_3$ aq., and brine), dried over magnesium sulfate, the solids were removed by filtration and the solvent of the filtrate was removed under reduced pressure. The crude intermediate was used without further purification in the next step.

Step 3. Preparation of (3S)—N-(4-Fluoro-3-methylphenyl)-1-{[(1-methylethyl)amino](oxo)acetyl}pyrrolidine-3-carboxamide (S)-ethyl 2-(3-((4-fluoro-3-methylphenyl)carbamoyl)-pyrrolidin-1-yl)-2-oxoacetate (300 mg) was dissolved in ethanol (8 mL) and to this was added isopropylamine (211 mg, 3.58 mmol) as a solution in ethanol (2 mL). After 3 hours isopropylamine (1 mL, 11.64 mmol) was added. The reaction mixture was stirred at room temperature in a closed vessel for 3 days. The solvents were removed under reduced pressure and the crude was purified by preparative HPLC (stationary phase: RP Vydac Denali C18, 10 μm, 200 g, 5 cm), mobile phase: 0.25% $NH_4HCO_3$ solution in water, $CH_3CN$). The fractions were pooled and the solvents were removed under reduced pressure to afford compound 4 as a white solid. Method A, Rt=1.35 min, m/z=336.4 $(M+H)^+$, exact mass: 335.2. $^1$H NMR (400 MHz, DMSO-$d_6$) δ ppm 1.02-1.16 (m, 12H), 1.93-2.20 (m, 4H), 2.18-2.22 (m, 6H), 3.04-3.24 (m, 2H), 3.40 (dt, J=12.1, 7.7 Hz, 1H), 3.48-3.60 (m, 2H), 3.60-3.72 (m, 2H), 3.73-3.85 (m, 2H), 3.85-4.01 (m, 3H), 6.97-7.14 (m, 2H), 7.33-7.43 (m, 2H), 7.46-7.61 (m, 2H), 8.44 (s, 1H), 8.46 (s, 1H), 10.02 (s, 1H), 10.05 (s, 1H), as a mixture of rotamers. Differential scanning calorimetry (From 30 to 300° C. at 10° C./min), Peak: 137.99° C.

Compound 5: (S)-1-(2-(cyclopentylamino)-2-oxoacetyl)-N-(4-fluoro-3-methylphenyl)-pyrrolidine-3-carboxamide

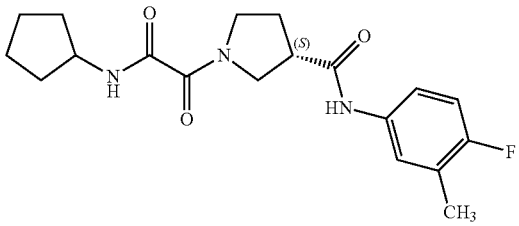

Compound 5 was made according to the method described for compound 4 with the exception that in step 3, cyclopentylamine (10 eq.) was employed instead of isopropylamine and the duration of the reaction at room temperature was two days instead of three. Method A, Rt=1.49 min, m/z=362.1 $(M+H)^+$, exact mass: 361.2. $^1$H NMR (400 MHz, DMSO-$d_6$) δ ppm 1.37-1.56 (m, 7H), 1.57-1.72 (m, 4H), 1.75-1.89 (m, 4H), 1.96-2.20 (m, 5H), 2.18-2.23 (m, 6H), 3.03-3.25 (m, 2H), 3.34-3.45 (m, 1H), 3.48-3.59 (m, 2H), 3.60-3.70 (m, 2H), 3.71-3.83 (m, 2H), 3.87-3.97 (m, 1H), 3.97-4.11 (m, 2H), 6.99-7.13 (m, 2H), 7.38 (dd, J=8.1, 3.7 Hz, 2H), 7.47-7.59 (m, 2H), 8.52 (s, 1H), 8.54 (s, 1H), 10.03 (s, 1H), 10.05 (s, 1H), as a mixture of rotamers. Differential scanning calorimetry (From 30 to 300° C. at 10° C./min), Peak: 163.50° C.

Compound 6: (S)—N-(4-fluoro-3-methylphenyl)-1-(2-(((R)-1-hydroxypropan-2-yl)amino)-2-oxoacetyl) pyrrolidine-3-carboxamide

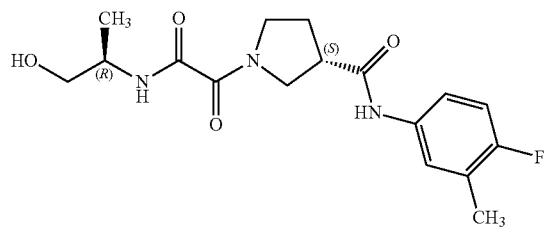

Compound 6 was made according to the method described for compound 4, with the exception that in step 3, (R)-2-aminopropanol (10 eq.) was employed instead of isopropylamine and the duration of the reaction at room temperature was two days instead of three. Method A, Rt=1.14 min, m/z=352.0 $(M+H)^+$, exact mass: 351.2. $^1$H NMR (400 MHz, DMSO-$d_6$) δ ppm 1.06 (d, J=6.6 Hz, 6H), 1.93-2.15 (m, 3H), 2.18-2.22 (m, 6H), 3.07-3.18 (m, 3H), 3.26-3.30 (m, 1H), 3.32-3.46 (m, 4H), 3.49-3.61 (m, 2H), 3.61-3.75 (m, 2H), 3.76-3.90 (m, 4H), 3.99 (dd, J=11.7, 7.7 Hz, 1H), 4.67-4.80 (m, 2H), 7.00-7.11 (m, 2H), 7.31-7.45 (m, 2H), 7.46-7.58 (m, 2H), 8.29 (s, 1H), 8.31 (s, 1H), 10.03 (s, 1H), 10.05 (s, 1H), as a mixture of rotamers.

Compound 7: (3S)—N-(4-Fluoro-3-methylphenyl)-1-{[(3-methyloxetan-3-yl)amino]-(oxo)acetyl}pyrrolidine-3-carboxamide

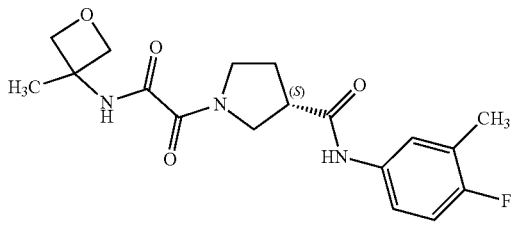

Compound 7 was made according to the method described for compound 4 with the exception that in step 3, 3-methyloxetan-3-amine (2 eq.) was employed instead of isopropylamine. The reaction proceeded at 50° C. for 1 week instead of at room temperature for three days as described for compound 4. Method B, Rt=0.73 min, m/z=364.4 (M+H)$^+$, exact mass: 363.2. $^1$H NMR (400 MHz, DMSO-d$_6$) δ ppm 1.49-1.56 (m, 6H), 1.93-2.22 (m, 5H), 2.19-2.21 (m, 6H), 3.07-3.25 (m, 2H), 3.37-3.47 (m, 2H), 3.50-3.60 (m, 2H), 3.62-3.75 (m, 2H), 3.76-3.89 (m, 2H), 3.98 (dd, J=11.6, 7.6 Hz, 1H), 4.27-4.35 (m, 4H), 4.60-4.70 (m, 4H), 7.01-7.11 (m, 1H), 7.35-7.45 (m, 1H), 7.49-7.57 (m, 2H), 9.20 (br. s., 1H), 9.25 (s, 1H), 10.10 (br. s., 1H), 10.12 (s, 1H), as a mixture of rotamers.

Compound 8: (3S)—N-(4-Fluoro-3-methylphenyl)-1-[{[(1R)-1-methylpropyl]amino}(oxo)acetyl]pyrrolidine-3-carboxamide

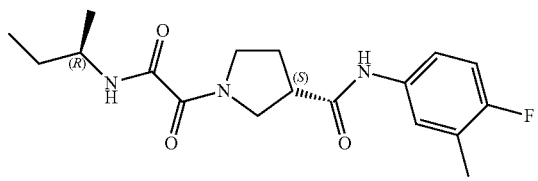

Compound 8 was made according to the method described for compound 4, with the exception that in step 3, (R)-butan-2-amine (2 eq.) was employed instead of isopropylamine. The duration of the reaction at room temperature was 18 hours instead of three days as described for compound 4. Method B, Rt=0.87 min, m/z=348.2 (M–H)$^-$, exact mass: 349.2. $^1$H NMR (400 MHz, DMSO-d$_6$) δ ppm 0.77-0.87 (m, 6H), 1.05-1.10 (m, 6H), 1.37-1.55 (m, 4H), 1.93-2.27 (m, 4H), 2.19-2.22 (m, 6H), 3.07-3.26 (m, 2H), 3.37-3.46 (m, 1H), 3.49-3.60 (m, 2H), 3.62-3.86 (m, 6H), 3.96 (dd, J=11.7, 7.7 Hz, 1H), 7.02-7.11 (m, 2H), 7.35-7.44 (m, 2H), 7.49-7.56 (m, 2H), 8.38 (s, 1H), 8.40 (s, 1H), 10.03 (s, 1H), 10.06 (s, 1H), as a mixture of rotamers.

Compound 9: (3S)—N-(4-Fluoro-3-methylphenyl)-1-{oxo[(3S)-tetrahydrofuran-3-ylamino]-acetyl}pyrrolidine-3-carboxamide

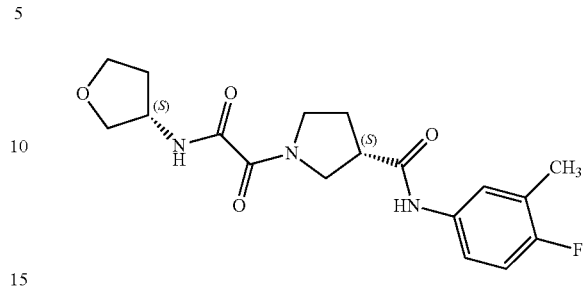

Compound 9 was made according to the method described for compound 4, with the exception that in step 3, (S)-tetrahydrofuran-3-amine (2 eq.) was employed instead of isopropylamine. The reaction proceeded at 50° C. for 2.5 days instead of at room temperature for three days as described for compound 4. Method B, Rt=0.72 min, m/z=364.1 (M+H)$^+$, exact mass: 363.2. $^1$H NMR (400 MHz, DMSO-d$_6$) δ ppm 1.80-1.91 (m, 2H), 1.96-2.26 (m, 6H), 2.19-2.21 (m, 6H), 3.07-3.23 (m, 2H), 3.36-3.45 (m, 1H), 3.47-3.59 (m, 4H), 3.61-3.73 (m, 4H), 3.74-3.85 (m, 6H), 3.93 (dd, J=11.4, 7.7 Hz, 1H), 4.20-4.35 (m, 2H), 7.01-7.12 (m, 2H), 7.33-7.45 (m, 2H), 7.47-7.57 (m, 2H), 8.80 (s, 1H), 8.82 (s, 1H), 10.03 (s, 1H), 10.05 (s, 1H), as a mixture of rotamers.

Compound 10: (2S,3S)—N-(4-Fluoro-3-methylphenyl)-2-methyl-1-{[(3-methyloxetan-3-yl)-amino](oxo)acetyl}pyrrolidine-3-carboxamide

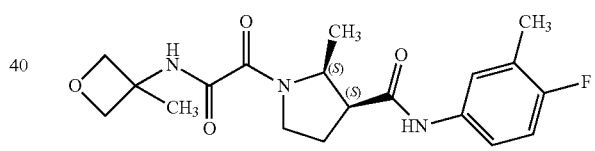

Step 1. Preparation of (9-methyl 2-methyl-1-(1-phenylethyl)-4,5-dihydro-1H-pyrrole-3-carboxylate The title compound was prepared according to methods provided in Tetrahedron Letters, Vol. 33, No. 30, pp. 4311-4312, 1992 and references cited therein.

Step 2. Preparation of (2S,3S)-methyl 2-methyl-1-((S)-1-phenyl ethyl)pyrrolidine-3-carboxylate To a solution of (S)-methyl 2-methyl-1-(1-phenylethyl)-4,5-dihydro-1H-pyrrole-3-carboxylate (5.92 g, 24.1 mmol) in acetonitrile (190 mL) was added acetic acid (2.07 mL, 36.2 mmol). The reaction mixture was cooled to 0° C. then sodium triacetoxyborohydride (7.67 g, 36.17 mmol) was added and stirring was continued at 0° C. for 3 hours. The solvent was removed under reduced pressure, the crude was reconstituted in CH$_2$Cl$_2$ and Na$_7$CO$_3$ (sat., aq.) was added. The mixture was stirred vigorously. The organic layer was removed, washed with water, then dried over magnesium sulfate. The solids were removed by filtration and the solvent of the filtrate was removed under reduced pressure.

The obtained crude oil was purified by silica gel column chromatography using a heptane/ethyl acetate gradient (100/0 to 70/30). The best fractions were pooled and the solvents were removed under reduced pressure. The oil was triturated in heptane to afford a white solid, (2S,3S)-methyl 2-methyl-1-((S)-1-phenylethyl)pyrrolidine-3-carboxylate. Method C, Rt=1.75 min, m/z=248.4 (M+H)$^+$, exact mass: 247.2. $^1$H NMR (chloroform-d) fits the data described in Tetrahedron Letters, Vol. 33, No. 30, pp. 4311-4312, 1992.

Step 3. Preparation of Lithium (2S,3S)-2-methyl-1-((S)-1-phenylethyl)pyrrolidine-3-carboxylate (2S,3S)-methyl 2-methyl-1-((S)-1-phenylethyl)pyrrolidine-3-carboxylate (100 mg, 0.40 mmol) was dissolved in THF (1.2 mL). To this was added lithium hydroxide (14 mg, 0.61 mmol) in distilled water (200 μL) and methanol (50 μL) and the mixture became clear. The resulting mixture was stirred for 18 hours. The solvent was removed under reduced pressure and the residue was used without further purification in the next step.

Step 4. Preparation of (2S,3S)—N-(4-fluoro-3-methylphenyl)-2-methyl-1-((S)-1-phenylethyl)-pyrrolidine-3-carboxamide 4-fluoro-3-methylaniline (253 mg, 2.02 mmol) was added to a mixture of lithium (2S,3S)-2-methyl-1-((S)-1-phenylethyl)pyrrolidine-3-carboxylate (472 mg), HATU (1.15 g, 3.03 mmol), and N,N-diisopropylethylamine (0.7 mL, 4.04 mmol) in CH$_2$Cl$_2$. The mixture stirred at room temperature for 1 hour. The solution was diluted in CH$_2$Cl$_2$ and water, the organic layer was removed, dried over MgSO$_4$ and solids were removed by filtration. The solvent was removed under reduced pressure and the crude was purified by silica gel chromatography using a heptane/ethyl acetate (100/0 to 70/30) gradient. The best fractions were pooled and the solvent removed under reduced pressure to afford a white solid, (2S,3S)—N-(4-fluoro-3-methylphenyl)-2-methyl-1-((S)-1-phenylethyl)pyrrolidine-3-carboxamide. Method C, Rt=1.87 min, m/z=341.2 (M+H)$^+$, exact mass: 340.2. $^1$H NMR (360 MHz, CHLOROFORM-d) δ ppm 1.26 (d, J=6.6 Hz, 3H), 1.36 (d, J=7.0 Hz, 3H), 1.82-1.97 (m, 1H), 2.02-2.18 (m, 1H), 2.26 (d, J=1.8 Hz, 3H), 2.56-2.73 (m, 2H), 2.76-2.88 (m, 1H), 2.88-2.99 (m, 1H), 4.08-4.25 (m, 1H), 6.85-6.98 (m, 1H), 7.22-7.45 (m, 7H), 9.52 (br. s., 1H)

Step 5. Preparation of (2S,3S)—N-(4-fluoro-3-methylphenyl)-2-methylpyrrolidine-3-carboxamide To a solution containing (2S,3S)—N-(4-fluoro-3-methylphenyl)-2-methyl-1-((S)-1-phenylethyl)pyrrolidine-3-carboxamide (395 mg, 1.16 mmol) in methanol (20 mL) was added 10% Pd/C (123 mg) under a nitrogen atmosphere. The reaction mixture was placed under hydrogen atmosphere and stirred for 24 hours. Hydrogen was removed, the reaction mixture was filtered through decalite, and the residue was concentrated under reduced pressure to afford a colorless oil which was used without further purification in the next step.

Step 6. Preparation of ethyl 2-((2S,3S)-3-((4-fluoro-3-methylphenyl)carbamoyl)-2-methylpyrrolidin-1-yl)-2-oxoacetate Ethyl oxalyl chloride (0.23 mL, 2.06 mmol) was added dropwise to a solution of (2S,3S)—N-(4-fluoro-3-methylphenyl)-2-methylpyrrolidine-3-carboxamide (244 mg, 1.03 mmol) and diisopropylethylamine (0.71 mL, 4.12 mmol) in anhydrous CH$_2$Cl$_2$ (10 mL) under nitrogen atmosphere at room temperature. The reaction mixture stirred at room temperature overnight. HCl (0.5 M, aq.) was added to the reaction mixture. The organic layer was removed, washed with NaHCO$_3$ (aq., sat.) and brine, dried over Na$_2$SO$_4$, the solids were removed by filtration and the solvent of the filtrate were removed under reduced. The residue was purified by silica gel column chromatography using a heptane/ethyl acetate (100/0 to 30/70) gradient to afford the title compound as an oil that was dried under vacuum at 50° C. for 2 hours and used without further purification.

Step 7. Preparation of 2-((2S,3S)-3-((4-fluoro-3-methylphenyl)carbamoyl)-2-methylpyrrolidin-1-yl)-2-oxoacetic acid To a solution of 2-((2S,3S)-3-((4-fluoro-3-methylphenyl)carbamoyl)-2-methylpyrrolidin-1-yl)-2-oxoacetate (204 mg, 0.61 mmol) in ethanol (5 mL) was added dropwise NaOH (1M aq., 1.82 mL). The reaction stirred at room temperature for 2 hours, then was diluted in CH$_2$Cl$_2$ and water. The layers were separated and the aqueous layer was acidified with HCl (1M aq.), the acid precipitated and was reconstituted in CH$_2$Cl$_2$. The aqueous layer was extracted with CH$_2$Cl$_2$. The combined organic layers were dried over Na$_2$SO$_4$, the solids were removed by filtration, and the solvent of the filtrate was removed under reduced pressure to afford the title compound. Method C, Rt=1.02 min, m/z=307.0 (M−H)$^-$, exact mass: 308.1.

Step 8. Preparation of (2S,3S)—N-(4-Fluoro-3-methylphenyl)-2-methyl-1-{[(3-methyloxetan-3-yl)amino](oxo)acetyl}pyrrolidine-3-carboxamide To a solution of 2-((2S,3S)-3-((4-fluoro-3-methylphenyl)carbamoyl)-2-methylpyrrolidin-1-yl)-2-oxoacetic acid (128 mg, 0.42 mmol), HATU (236.79 mg, 1.5 eq) and DIPEA (145 μL, 2 eq) in CH$_2$Cl$_2$ (5 mL) was added 3-methyloxetan-3-amine (36 mg, 0.42 mmol) and the reaction mixture was stirred overnight at room temperature. To the reaction mixture was added CH$_2$Cl$_2$ and HCl (1M, aq.). The layers were separated and the organic layer was washed with NaHCO$_3$ (sat., aq.) and brine. The combined organic layers were dried over Na$_2$SO$_4$, the solids were removed by filtration and the filtrate was concentrated under reduced pressure. The crude was purified by preparative HPLC (stationary phase: RP X-Bridge Prep C18 OBD-10 μm, 30×150 mm), mobile phase: 0.25% NH$_4$HCO$_3$ solution in water, CH$_3$CN). The best fractions were pooled and the solvent was removed under reduced pressure to afford the title compound 10.

Method C, Rt=1.46 min, m/z=376.0 (M−H)$^-$, exact mass: 377.2. $^1$H NMR (400 MHz, DMSO-d$_6$) δ ppm 0.99-1.05 (m, 6H), 1.53 (m, J=4.2 Hz, 6H), 1.86-2.05 (m, 2H), 2.18-2.23 (m, 6H), 2.25-2.36 (m, 2H), 3.02-3.23 (m, 2H), 3.38-3.70 (m, 3H), 3.83-3.95 (m, 1H), 4.27-4.35 (m, 4H), 4.46-4.57 (m, 1H), 4.60-4.66 (m, 4H), 4.81-4.94 (m, 1H), 6.99-7.12 (m, 2H), 7.33-7.42 (m, 2H), 7.45-7.55 (m, 2H), 9.17 (s, 1H), 9.26 (s, 1H), 9.94 (s, 1H), 10.00 (s, 1H), as a 1/1 mixture of rotamers.

Compound 11: (S)—N-(3-chloro-4,5-difluorophenyl)-1-(2-oxo-2-(((R)-1,1,1-trifluoropropan-2-yl)amino)acetyl)pyrrolidine-3-carboxamide

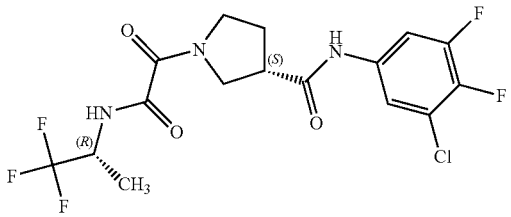

Compound 11 was made according to the method described for compound 1, step one, with the exception that 3-chloro-4,5-difluoroaniline was employed instead of 3-bromo-4,5-difluoroaniline. The coupling reaction to afford the title compound was done according to the procedure described for compound 13, step two, with the exception that (R)-1,1,1-trifluoro-2-propylamine was employed instead of 1-(trifluoromethyl)-cyclopropanamine. Method B, Rt=1.02 min, m/z=426.1 (M−H)⁻, exact mass: 427.1. $^1$H NMR (400 MHz, DMSO-$d_6$) δ ppm 1.30 (d, J=7.0 Hz, 3H) 1.98-2.28 (m, 2H) 3.07-3.27 (m, 1H) 3.41-4.04 (m, 4H) 4.54-4.75 (m, 1H) 7.46-7.72 (m, 2H) 9.17-9.33 (m, 1H) 10.43 (m, 1H), as a mixture of rotamers.

Compound 12: (3S)—N-(4-Fluoro-3-methylphenyl)-1-{[(1-methylethyl)amino](oxo)-acetyl}piperidine-3-carboxamide

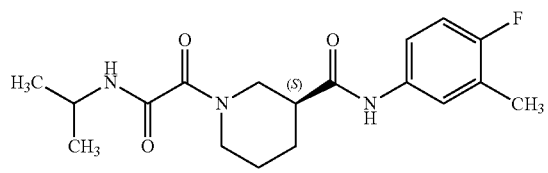

Step 1. Preparation of (S)-tert-butyl 3-((4-fluoro-3-methylphenyl) carbamoyl)piperidine-1-carboxylate A mixture of (S)-1-boc-piperidine-3-carboxylic acid CAS [88495-54-9] (9 g, 39.3 mmol), 4-fluoro-3-methylaniline (4.91 g, 39.3 mmol), and $CH_2Cl_2$ (90 mL) was cooled to 0° C. followed by the addition of diisopropylethylamine (20.5 mL, 117.8 mmol) and HATU (17.9 g, 47.1 mmol). The reaction mixture stirred at 0° C. for 2 hours followed by the addition of citric acid (sat., aq., 100 mL), $NaHCO_3$ (sat., aq., 100 mL), and brine. The organic layer was dried over $Na_2SO_4$, the solids were removed by filtration and the solvents were removed under reduced pressure. The crude was purified using a petroleum ether/ethyl acetate gradient (from 100/1 to 3/1). The best fractions were pooled and the solvent was removed under reduced pressure. $^1$H NMR (400 MHz, CHLOROFORM-d) δ ppm 1.26-1.37 (m, 1H), 1.39 (s, 9H), 1.59 (qd, J=12.1, 3.4 Hz, 1H), 1.69 (d, J=13.2 Hz, 1H), 1.91 (d, J=12.6 Hz, 1H), 2.19 (d, J=1.8 Hz, 3H), 2.40 (tt, J=11.0, 3.7 Hz, 1H), 2.75 (t, J=11.7 Hz, 1H), 2.97 (br. s., 1H), 3.86 (d, J=13.1 Hz, 1H), 4.03 (br. s., 1H), 7.05 (t, J=9.3 Hz, 1H), 7.31-7.42 (m, 1H), 7.51 (dd, J=7.0, 2.3 Hz, 1H), 9.97 (s, 1H)

Subsequent deprotection of the boc group was possible via addition of $CH_2Cl_2$ (100 mL) and HCl (100 mL, in dioxane) at room temperature for 24 hours to afford the (S)—N-(4-fluoro-3-methylphenyl)piperidine-3-carboxamide hydrochloride intermediate.

$^1$H NMR (400 MHz, CHLOROFORM-d) δ ppm 1.49-1.87 (m, 3H), 1.95-2.08 (m, 1H), 2.19 (d, J=2.0 Hz, 3H), 2.80-2.93 (m, 2H), 3.00 (q, J=10.4 Hz, 1H), 3.17 (d, J=12.0 Hz, 1H), 3.29 (d, J=11.0 Hz, 1H), 7.07 (t, J=9.2 Hz, 1H), 7.35-7.45 (m, 1H), 7.52 (dd, J=7.0, 2.3 Hz, 1H), 8.90 (d, J=11.2 Hz, 1H), 9.12 (m, J=9.5 Hz, 1H), 10.31 (s, 1H)

Step 2

The preparation of compound 12 followed analogous procedures as in the synthesis step 2 of compound 4 with the exception that (S)—N-(4-fluoro-3-methylphenyl)piperidine-3-carboxamide hydrochloride was employed in the reaction with ethyl chlorooxoacetate instead of (S)—N-(4-fluoro-3-methylphenyl)pyrrolidine-3-carboxamide hydrochloride. Then, as in the subsequent step three in the method described for compound 4, isopropylamine was used in a closed vessel to afford compound 12. Method C, Rt=1.47 min, m/z=350.2 (M+H)⁺, exact mass: 349.2. $^1$H NMR (400 MHz, DMSO-$d_6$) δ ppm 1.03-1.12 (m, 12H) 1.30-1.52 (m, 2H) 1.60-1.71 (m, 2H) 1.71-1.81 (m, 2H) 1.92-2.09 (m, 2H) 2.17-2.21 (m, 6H) 2.38-2.46 (m, 1H) 2.53-2.58 (m, 1H) 2.69-2.81 (m, 2H) 3.03 (t, J=11.5 Hz, 1H) 3.26 (dd, J=13.3, 10.5 Hz, 1H) 3.68 (d, J=13.3 Hz, 1H) 3.77 (d, J=13.3 Hz, 1H) 3.83-3.96 (m, 2H) 4.18 (d, J=12.9 Hz, 1H) 4.36 (d, J=12.9 Hz, 1H) 7.02-7.09 (m, 2H) 7.33-7.44 (m, 2H) 7.50 (d, J=6.9 Hz, 2H) 8.47-8.58 (m, 2H) 9.96 (s, 2H), a mixture of rotamers.

Compound 13: (S)—N-(3-chloro-4,5-difluorophenyl)-1-(2-oxo-2-((1-(trifluoromethyl) cyclopropyl)amino)acetyl)pyrrolidine-3-carboxamide

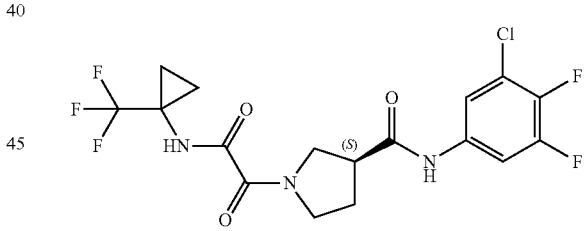

Step 1. Preparation of (S)-t-butyl 3-((3-chloro-4,5-difluorophenyl)carbamoyl) pyrrolidine-1-carboxylate The title compound was prepared according to the procedure in step 1 of compound 1 with the exception that 3-chloro-4,5-difluoroaniline was employed instead of 3-bromo-4,5-difluoroaniline. Boc group deprotection and reaction with ethyl chlorooxoacetate then proceed according to the methods described.

Step 2. Preparation of (S)—N-(3-chloro-4,5-difluorophenyl)-1-(2-oxo-2-((1-(trifluoromethyl) cyclopropyl)amino)acetyl)pyrrolidine-3-carboxamide A solution of (S)-2-(3-(3-chloro-4,5-difluorophenyl)carbamoyl)pyrrolidin-1-yl)-2-oxoacetic acid (0.33 g, 0.99 mmol) in DMF (10 mL) was cooled to 5° C. Then diisopropylethylamine (0.513 mL, 2.98 mmol) and 1-(trifluoromethyl)-cyclopropanamine (0.092 mL, 0.992 mmol) were added and stirred at 5° C. A solution of HATU (0.414 g, 1.091 mmol) in DMF (2 mL) was added dropwise at 5° C. The solution was stirred at 5° C. for 1 h. The reaction quenched with water and neutralised with HCl (1M, aq.), brine (15 mL) was added and the compound was extracted with ethyl acetate. The organic layer was removed, dried with MgSO$_4$, the solids were removed by filtration and the solvents removed under reduced pressure to afford a solid. The solid was dissolved in CH$_3$CN with heat and cooled to ambient temperature. The precipitate was removed by filtration and the filtrate was concentrated under reduced pressure. The crude was purified by silica flash column chromatography using a heptane/ethyl acetate gradient (30/70 to 0/100). The desired fractions were collected and evaporated to dryness to afford compound 13 as a white solid. Method B, Rt=1.02 min, m/z=438.1 (M−H)$^-$, exact mass: 439.1. $^1$H NMR (400 MHz, DMSO-d$_6$) δ ppm 1.04-1.13 (m, 2H) 1.22-1.31 (m, 2H) 1.97-2.27 (m, 2H) 3.09-3.24 (m, 1H) 3.36-4.00 (m, 4H) 7.49-7.72 (m, 2H) 9.44 (s, 1H) 10.43 (br. s., 1H), as a mixture of rotamers.

Compound 14: (S)—N-(4-fluoro-3-(trifluoromethyl)phenyl)-1-(2-oxo-2-(((R)-1,1,1-trifluoropropan-2-yl)amino)acetyl)pyrrolidine-3-carboxamide

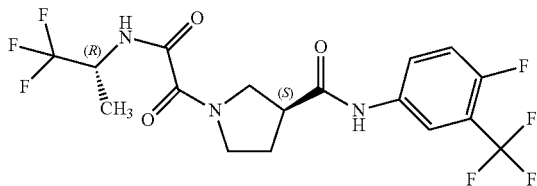

Compound 14 was made according to the method described for compound 1, with the exception that, in step 1, 4-fluoro-3-(trifluoromethyl)aniline was employed instead of 3-bromo-4,5-difluoroaniline. The coupling reaction to afford the title compound was done according to the procedure described for compound 13, step two, with the exception that (R)-1,1,1-trifluoro-2-propylamine was employed instead of 1-(trifluoromethyl)-cyclopropanamine. Method B, Rt=1.01 min, m/z=442.1 (M–H), exact mass: 443.1. $^1$H NMR (400 MHz, DMSO-d$_6$) δ ppm 1.30 (d, J=7.0 Hz, 3H), 1.87-2.37 (m, 2H), 3.13-3.27 (m, 1H), 3.37-3.98 (m, 4H), 4.34-4.77 (m, 1H), 7.41-7.55 (m, 1H), 7.76-7.90 (m, 1H), 8.01-8.25 (m, 1H), 9.27 (br. s., 1H), 10.50 (br. s., 1H)

Compound 15: (S)—N-(3-chloro-4-fluorophenyl)-1-(2-oxo-2-(((R)-1,1,1-trifluoropropan-2-yl)amino)acetyl)pyrrolidine-3-carboxamide

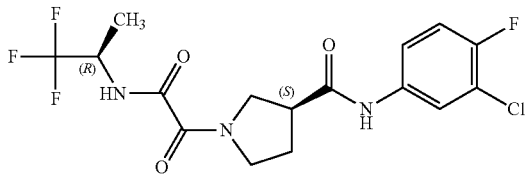

Compound 15 was made according to the methods described for the synthesis of compound 1, with the exception that, in step one, 3-chloro-4-fluoroaniline was used instead of 3-bromo-4,5-difluoroaniline. The coupling reaction to afford the title compound was done according to the procedure described for compound 13, step two, with the exception that (R)-1,1,1-trifluoro-2-propylamine was employed instead of 1-(trifluoromethyl)-cyclopropanamine. Method B, Rt=0.96 min, m/z=408.1 (M−H)$^-$, exact mass: 409.1. $^1$H NMR (400 MHz, DMSO-d$_6$) δ ppm 1.30 (d, J=7.0 Hz, 3H), 1.91-2.30 (m, 2H), 3.10-3.27 (m, 1H), 3.38-4.02 (m, 4H), 4.52-4.71 (m, 1H), 7.32-7.41 (m, 1H), 7.43-7.51 (m, 1H), 7.86-7.99 (m, 1H), 9.26 (br. s., 1H), 10.34 (br. s., 1H), a mixture of rotamers.

Compound 16: (S)—N-(3-chloro-4,5-difluorophenyl)-1-(2-oxo-2-((1,1,1-trifluoro-2-methylpropan-2-yl)amino)acetyl)pyrrolidine-3-carboxamide

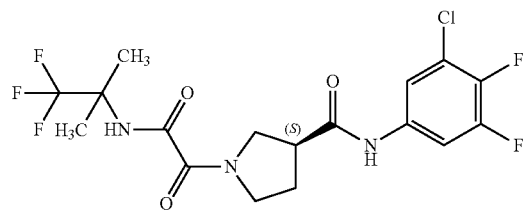

Compound 16 was prepared according to the method to prepare compound 13 with the exception that 1,1,1-trifluoro-2-methylpropan-2-amine was employed in step two, instead of 1-(trifluoromethyl)-cyclopropanamine. Method B, Rt=1.08 min, m/z=440.1 (M−H)$^-$, exact mass: 441.1. $^1$H NMR (400 MHz, DMSO-d$_6$) δ ppm 1.54 (s, 6H) 1.98-2.31 (m, 2H) 3.06-3.28 (m, 1H) 3.40-3.97 (m, 4H) 7.50-7.80 (m, 2H) 8.56 (m, 1H) 10.44 (br. s., 1H), as a mixture of rotamers.

Synthesis of compound 17: N-(4-fluoro-3-methylphenyl)-5-methyl-1-(2-((3-methyloxetan-3-yl)amino)-2-oxoacetyl)pyrrolidine-3-carboxamide

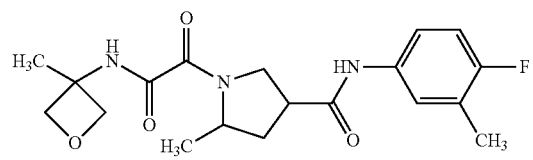

Step 1. Preparation of 1-(t-butoxycarbonyl)-5-methylpyrrolidine-3-carboxylic acid The title compound was prepared as a mixture of diastereomers according to methods found in WO2010059658 (p 211), starting from methyl 2-chloro-5-methyl-1H-pyrrole-3-carboxylate which is described in Foley, L., Tetrahedron Letters 1994, vol. 35, p. 5989.

Step 2. Preparation of t-butyl 4-((4-fluoro-3-methylphenyl)carbamoyl)-2-methylpyrrolidine-1-carboxylate 4-fluoro-3-methylaniline (1.09 g, 8.72 mmol) was added to a solution of 1-(t-butoxycarbonyl)-5-methylpyrrolidine- 3-carboxylic acid (2 g, 8.72 mmol), DIPEA (4.33 mL, 26.17 mmol), and HATU (4.98 g, 14.09 mmol) in CH$_2$Cl$_2$ (50 mL). The reaction mixture stirred for 1 h at room temperature, then partitioned with water. The organic layer was removed, dried over MgSO$_4$, the solids were removed by filtration, and the solvent of the filtrate was removed under reduced pressure. The crude was purified via silica gel column chromatography resulting in the title compound. Method C, Rt=1.96 min, m/z=335.0 (M–H)$^-$, and 1.98 min, m/z=335.1 (M–H)$^-$ exact mass: 336.2.

Step 3. Preparation of ethyl 2-(4-((4-fluoro-3-methylphenyl)carbamoyl)-2-methylpyrrolidin-1-yl)-2-oxoacetate To a solution of t-butyl 4-((4-fluoro-3-methylphenyl)carbamoyl)-2-methylpyrrolidine-1-carboxylate in CH$_2$Cl$_2$ under an atmosphere of nitrogen was added TFA dropwise. The reaction mixture stirred at room temperature for 2 hours. The solvent was removed under reduced pressure and the crude was reconstituted in CH$_2$Cl$_2$ and NaOH (1 M, aq.). The mixture was stirred vigorously for 5 minutes. The layers were separated and the aqueous layer was extracted with CH$_2$Cl$_2$. The combined organic layers were dried over MgSO$_4$, the solids were removed by filtration and the filtrate was concentrated under reduced pressure to afford an oil. To this oil was added anhydrous CH$_2$Cl$_2$ (50 mL), and triethylamine (1.09 g, 7.83 mmol). To the resulting solution was added ethyl oxalyl chloride (0.44 mL, 3.92 mmol) dropwise at room temperature, then stirred for 18 hours. HCl (0.5 M aq.) was added to the reaction mixture. The organic layer was removed, dried over MgSO$_4$, the solids were removed by filtration and the filtrate was concentrated to afford an oil, dried under vacuum at 50° C. for 4 hours and used without further purification.

Step 4. Preparation of 2-(4-((4-fluoro-3-methylphenyl)carbamoyl)-2-methylpyrrolidin-1-yl)-2-oxoacetic acid The ester hydrolysis of ethyl 2-(4-((4-fluoro-3-methylphenyl)carbamoyl)-2-methylpyrrolidin-1-yl)-2-oxoacetate was achieved according to the method described in step 7 of compound 10.

Step 5. Preparation of N-(4-fluoro-3-methylphenyl)-5-methyl-1-(2-((3-methyloxetan-3-yl)amino)-2-oxoacetyl)pyrrolidine-3-carboxamide The title compound was prepared according to the procedure in step 8 in the synthesis of compound 10. Isomers were isolated via preparative SFC (stationary phase: Whelk-0 (R, R) 20×250 mm), mobile phase: CO$_2$, EtOH/iPrOH (50/50) with 0.2% iPrNH$_2$). The desired fractions were collected, and the solvent was removed under reduced pressure to afford compounds 17a (119 mg), 17b (116 mg), 17c (78 mg), and 17d (94 mg) named in order of elution.

| Compound | LC-MS Method, Rt (min) | m/z (M + H)$^+$ | Configuration |
|---|---|---|---|
| 17a | C, 1.39 | 378.2 | (3R,5S) or (3S,5R) |
| 17b | C, 1.39 | 378.2 | (3R,5S) or (3S,5R) |
| 17c | C, 1.37 | 378.2 | (3S,5S) or (3R,5R) |
| 17d | C, 1.37 | 378.2 | (3S,5S) or (3R,5R) |

Compound 17a: $^1$H NMR (600 MHz, DMSO-d$_6$) δ ppm 1.21 (d, J=6.3 Hz, 3H), 1.26 (d, J=6.2 Hz, 3H), 1.53 (s, 3H), 1.54 (s, 3H), 1.75 (ddd, J=12.7, 10.1, 8.1 Hz, 1H), 1.87 (ddd, J=13.0, 7.5, 5.6 Hz, 1H), 2.19-2.22 (m, 6H), 2.41 (dt, J=12.6, 7.5 Hz, 1H), 2.46-2.53 (m, 1H), 3.01-3.12 (m, 2H), 3.52 (dd, J=12.2, 7.9 Hz, 1H), 3.65 (dd, J=11.4, 9.8 Hz, 1H), 3.90 (dd, J=12.2, 8.1 Hz, 1H), 4.01-4.07 (m, 1H), 4.09 (dd, J=11.4, 7.5 Hz, 1H), 4.29-4.35 (m, 4H), 4.37-4.48 (m, 1H), 4.62-4.67 (m, 4H), 7.05-7.09 (m, 2H), 7.37-7.42 (m, 2H), 7.49-7.53 (m, 2H), 9.19 (s, 1H), 9.23 (s, 1H), 10.02 (s, 1H), 10.04 (s, 1H), as a mixture of rotamers.

Compound 17b: $^1$H NMR (400 MHz, DMSO-d$_6$) δ ppm 1.21 (d, J=6.2 Hz, 3H), 1.26 (d, J=6.2 Hz, 3H), 1.49-1.56 (m, 6H), 1.75 (ddd, J=12.7, 10.0, 8.0 Hz, 1H), 1.87 (ddd, J=13.0, 7.4, 5.8 Hz, 1H), 2.17-2.23 (m, 6H), 2.41 (dt, J=12.7, 7.5 Hz, 1H), 2.45-2.54 (m, 1H), 2.96-3.13 (m, 2H), 3.52 (dd, J=12.1, 7.9 Hz, 1H), 3.65 (dd, J=11.4, 9.8 Hz, 1H), 3.91 (dd, J=12.2, 8.0 Hz, 1H), 3.98-4.15 (m, 2H), 4.27-4.36 (m, 4H), 4.37-4.49 (m, 1H), 4.59-4.70 (m, 4H), 7.07 (t, J=9.1 Hz, 2H), 7.34-7.44 (m, 2H), 7.46-7.55 (m, 2H), 9.18 (s, 1H), 9.22 (s, 1H), 10.01 (s, 1H), 10.03 (br. s., 1H), as a mixture of rotamers.

Compound 17c: $^1$H NMR (400 MHz, DMSO-d$_6$) δ ppm 1.13-1.27 (m, 6H), 1.51 (s, 3H), 1.53 (s, 3H), 1.86 (ddd, J=12.3, 6.8, 2.9 Hz, 1H), 1.98 (dd, J=12.0, 6.9 Hz, 1H), 2.07-2.17 (m, 2H), 2.18-2.23 (m, 6H), 3.26-3.31 (m, 2H), 3.58-3.70 (m, 2H), 3.84 (dd, J=11.7, 7.9 Hz, 1H), 3.92-4.01 (m, 1H), 4.17-4.26 (m, 1H), 4.27-4.36 (m, 4H), 4.54-4.62 (m, 1H), 4.61-4.66 (m, 4H), 7.01-7.12 (m, 2H), 7.32-7.43 (m, 2H), 7.47-7.57 (m, 2H), 9.17 (s, 1H), 9.20 (s, 1H), 10.03 (s, 1H), 10.07 (s, 1H), as a mixture of rotamers.

Compound 17d: $^1$H NMR (600 MHz, DMSO-d$_6$) δ ppm 1.20 (d, J=6.5 Hz, 3H), 1.21 (d, J=6.5 Hz, 3H), 1.51 (s, 3H), 1.53 (s, 3H), 1.86 (ddd, J=12.3, 6.8, 2.9 Hz, 1H), 1.98 (dd, J=12.1, 6.8 Hz, 1H), 2.10-2.18 (m, 2H), 2.18-2.23 (m, 6H), 3.28-3.32 (m, 2H), 3.60-3.68 (m, 2H), 3.84 (dd, J=11.6, 7.9 Hz, 1H), 3.97 (dd, J=11.7, 7.8 Hz, 1H), 4.18-4.26 (m, 1H), 4.28-4.35 (m, 4H), 4.56-4.61 (m, 1H), 4.62-4.67 (m, 4H), 7.03-7.11 (m, 2H), 7.35-7.42 (m, 2H), 7.48-7.55 (m, 2H), 9.19 (s, 1H), 9.22 (s, 1H), 10.04 (s, 1H), 10.09 (s, 1H), as a mixture of rotamers.

Compound 18: N-(3-chloro-4,5-difluoro-phenyl)-2,2-dimethyl-1-[2-oxo-2-[[(1R)-2,2,2-trifluoro-1-methyl-ethyl]amino]acetyl]pyrrolidine-3-carboxamide

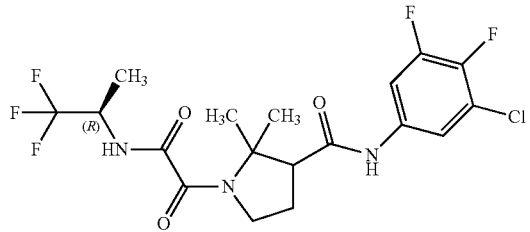

A mixture of diethyl fumarate (19.05 mL/113.848 mmol) and 2-nitropropane (10.2 mL/113.8 mmol) was treated with KF/basic alumina (20 g). The reaction mixture was stirred overnight and the mixture was filtered. The filtrate was concentrated yielding crude diethyl 2-(1-methyl-1-nitroethyl)butanedioate (20 g) which was used as such.

$^1$H NMR (400 MHz, DMSO-d$_6$) δ ppm 1.10-1.22 (m, 6H) 1.54 (s, 3H) 1.58 (s, 3H) 2.55-2.76 (m, 2H) 3.52 (dd, J=11.00, 3.96 Hz, 1H) 3.99-4.13 (m, 4H). To a solution of crude diethyl 2-(1-methyl-1-nitro-ethyl)butanedioate (2200 mg, 8.42 mmol), triethyl amine (1.17 mL/8.42 mmol) and ethanol (100 mL) was added Pd/C (10%) (448.04 mg/0.421 mmol) under a nitrogen flow. The resulting mixture was stirred under hydrogen atmosphere at ambient temperature until 3 equivalents of hydrogen were absorbed. The catalyst was removed by filtration over dicalite and the filtrate was evaporated to yield of ethyl 2,2-dimethyl-5-oxo-pyrrolidine-3-carboxylate (1.05 g) as a solid which was used as such. A mixture of ethyl 2,2-dimethyl-5-oxo-pyrrolidine-3-carboxylate (750 mg/4.05 mmol) and lawesson's reagent (983 mg/2.43 mmol) in toluene on molecular sieves (15 mL) was warmed to 70° C. for 1 hour, cooled and concentrated in vacuo, resulting in a solid residue. The crude was purified using silica gel column chromatography (gradient elution: EtOAc-heptane 0:100 to 100:0) yielding ethyl 2,2-dimethyl-5-thioxo-pyrrolidine-3-carboxylate (432 mg) as a slightly yellow powder, which was used as such. Method B, Rt=0.66 min, m/z=202.1 (M+H)$^+$, exact mass: 201.1. Ethyl 2,2-dimethyl-5-thioxo-pyrrolidine-3-carboxylate (100 mg, 0.5 mmol) was dissolved in tetrahydrofuran (2 mL). To this was added ethanol (2 mL) and the mixture was stirred overnight. The mixture was filtered over a path of dicalite, rinsed with ethanol and concentrated in vacuo yielding crude ethyl 2,2-dimethylpyrrolidine-3-carboxylate (50 mg) as a beige powder which was used as such.

Ethyl oxalyl chloride (65.35 µL/0.58 mmol) was added drop wise to a solution of crude ethyl 2,2-dimethylpyrrolidine-3-carboxylate (50 mg, 0.29 mmol) and DIPEA (0.25 mL/1.46 mmol) in CH$_2$Cl$_2$ (2 mL) at room temperature. The reaction mixture was stirred at room temperature for 1 hour. Saturated aqueous NaHCO$_3$ (5 mL) and CH$_2$Cl$_2$ (5 mL) was added to the reaction mixture and the layers were separated. The organic layer was dried on MgSO$_4$, filtered, and evaporated to dryness. The obtained residue was purified by silica gel column chromatography using gradient elution from heptane to EtOAc. (100:0 to 0:100). The desired fractions were concentrated in vacuo yielding ethyl 1-(2-ethoxy-2-oxo-acetyl)-2,2-dimethyl-pyrrolidine-3-carboxylate (80 mg) as a clear colorless oil which was used as such. Ethyl 1-(2-ethoxy-2-oxo-acetyl)-2,2-dimethyl-pyrrolidine-3-carboxylate (80 mg, 0.29 mmol) was dissolved in ethanol (1 mL/17.13 mmol) and cooled on an ice bath. NaOH (0.59 mL/1 M/0.59 mmol) was added, and the mixture was stirred while cooling was continued for 10 minutes. HCl (0.59 mL, 1 M, 0.59 mmol) was added drop wise under cooling. The mixture was concentrated in vacuo. The residue was partioned between water and Me-THF. The organic layer was separated, dried (Na$_2$SO$_4$), filtered and concentrated in vacuo, resulting in 2-(3-ethoxycarbonyl-2,2-dimethyl-pyrrolidin-1-yl)-2-oxo-acetic acid (70 mg) as an oil which was used as such. A solution of 2-(3-ethoxycarbonyl-2,2-dimethyl-pyrrolidin-1-yl)-2-oxo-acetic acid (70 mg, 0.29 mmol) in DMF (10 mL) was cooled to 5° C. in an ice-water bath. Then DIPEA (0.15 mL, 0.75 g/mL, 0.86 mmol) and (R)-1,1,1-trifluoro-2-propylamine (39.05 mg, 0.35 mmol) were added and stirred. A solution of HATU (120.36 mg, 0.32 mmol) in DMF (5 mL) was added drop wise while cooling was continued. The obtained solution was stirred for 1 hour under cooling. The reaction was quenched with water and neutralised with a 1N HCl solution. Brine (10 mL) was added and the compound was extracted with EtOAc (3×20 mL). The combined organics were dried with Na$_2$SO$_4$, filtered and evaporated to dryness. This was purified by flash column chromatography over silica Heptane to EtOAc (100/0-0/100). The desired fractions were collected and evaporated to dryness to afford ethyl 2,2-dimethyl-1-[2-oxo-2-[[(1R)-2,2,2-trifluoro-1-methyl-ethyl]amino]acetyl]pyrrolidine-3-carboxylate (70 mg) as a white solid which was used as such. Ethyl 2,2-dimethyl-1-[2-oxo-2-[[(1R)-2,2,2-trifluoro-1-methyl-ethyl]amino]acetyl]pyrrolidine-3-carboxylate (70 mg, 0.21 mmol) was dissolved in THF (5 mL). To this was added LiOH (17.7 mg, 0.74 mmol) in water (5 mL). MeOH (0.2 mL) was added to dissolve all the reactants. The mixture was stirred overnight at room temperature. Then it was concentrated in vacuo until only water remained. Next, HCl (0.74 mL, 1 M, 0.74 mmol) was added and this was extracted using Me-THF (3×10 mL). The combined extracts were washed with of brine (20 mL), dried on Na$_2$SO$_4$, filtered and concentrated in vacuo yielding 2,2-dimethyl-1-[2-oxo-2-[[(1R)-2,2,2-trifluoro-1-methyl-ethyl]amino]acetyl]pyrrolidine-3-carboxylic acid (45 mg) as a white powder which was used as such. 2,2-dimethyl-1-[2-oxo-2-[[(1R)-2,2,2-trifluoro-1-methyl-ethyl]amino]acetyl]pyrrolidine-3-carboxylic acid (45 mg, 0.15 mmol), 3-chloro-4,5-difluoro-aniline (58.02 mg, 0.29 mmol), HATU (110.3 mg, 0.29 mmol) and DIPEA (0.12 mL, 0.75 g/mL, 0.73 mmol) were dissolved in DMF (0.34 mL, 4.34 mmol). This mixture was stirred at room temperature for 2 hours. Extra DIPEA (0.12 mL, 0.75 g/mL, 0.73 mmol) was added and the mixture was shaken at 60° C. for 2 hours. This mixture was purified by silica gel column chromatography using gradient elution from heptane to EtOAc. (100:0 to 0:100) and further via preperative HPLC (Stationary phase: Uptisphere C18 ODB—10 µm, 200 g, 5 cm, Mobile phase: 0.25% NH$_4$HCO$_3$ solution in water, MeOH) The desired fractions were concentrated in vacuo, co-evaporated twice using MeOH and dried in a vacuum oven at 55° C. for 24 hours yielding N-(3-chloro-4,5-difluoro-phenyl)-2,2-dimethyl-1-[2-oxo-2-[[(1R)-2,2,2-trifluoro-1-methyl-ethyl]amino]acetyl]pyrrolidine-3-carboxamide (6.3 mg) as a white solid. $^1$H NMR (400 MHz, CHLOROFORM-d) δ ppm 1.35-1.39 (m, 3H), 1.46-1.49 (m, 3H), 1.69-1.80 (m, 3H), 2.01-2.20 (m, 1H), 2.23-2.43 (m, 1H), 2.58-2.74 (m, 1H), 3.86-4.09 (m, 1H), 4.20-4.47 (m, 1 H), 4.48-4.67 (m, 1H), 7.08 (s, 1H), 7.28-7.36 (m, 1H), 7.41-7.49 (m, 1H), 7.49-7.65 (m, 1H). LC method B; Rt: 1.11 min. m/z: 454.2 (M−H)− Exact mass: 455.1

Compound 19: (3S)-1-[2-(tert-butylamino)-2-oxo-acetyl]-N-(3-chloro-2,4-difluoro-phenyl)pyrrolidine-3-carboxamide

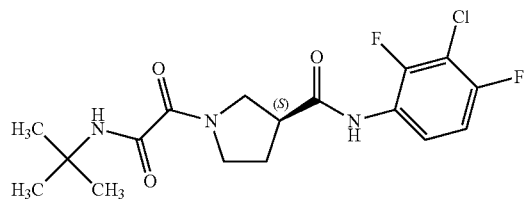

Ethyl 2-[(3S)-3-[(3-chloro-2,4-difluoro-phenyl)carbamoyl]pyrrolidin-1-yl]-2-oxo-acetate was obtained similar as described for (9-ethyl 2-(3-((3-bromo-4,5-difluorophenyl)carbamoyl) pyrrolidin-1-yl)-2-oxoacetate using 3-chloro-2,4-difluoro-aniline instead of 3-bromo-4,5-difluoroaniline in step one. Ethyl 2-[(3S)-3-[(3-chloro-2,4-difluoro-phenyl)carbamoyl]pyrrolidin-1-yl]-2-oxo-acetate (0.6 g, 1.66 mmol) was dissolved in tetrahydrofuran (15 mL). To this was added tert-butylamine (0.18 g, 2.49 mmol) and this mixture was cooled in an ice-water bath. Then lithium bis(trimethylsilyl)amide (1M in toluene) (4.99 mL, 1 M, 4.99 mmol) was added drop wise over a period of 5 minutes. The resulting mixture was stirred for 1 hour while cooling was continued. Then it was quenched using NH₄Cl (saturated/50 mL). This was extracted using EtOAc (3×50 mL). The combined extracts were washed with brine (50 mL), dried on Na₂SO₄, filtered and concentrated under reduced pressure. The obtained residue was purified by silica gel column chromatography using gradient elution from heptane to EtOAc. (100:0 to 0:100) and further via Prep HPLC (Stationary phase: RP)(Bridge Prep C18 OBD-10 μm, 30×150 mm, Mobile phase: 0.25% NH₄HCO₃ solution in water, MeOH) yielding compound 19 (136 mg) as a white powder. Method B, Rt=0.95 min, m/z=386.2 (M−H)⁻, Exact mass: 387.1. ¹H NMR (400 MHz, DMSO-d₆) δ ppm 1.31 (s, 9H), 1.85-2.30 (m, 2H), 3.15-4.33 (m, 5H), 7.26-7.34 (m, 1H), 7.65-7.86 (m, 1H), 8.00 (m, 1H), 10.08 (br. s., 1H) as a mixture of rotamers.

Compound 20: (3S)-1-[2-(tert-butylamino)-2-oxo-acetyl]-N-(3-cyano-4-fluorophenyl)-pyrrolidine-3-carboxamide

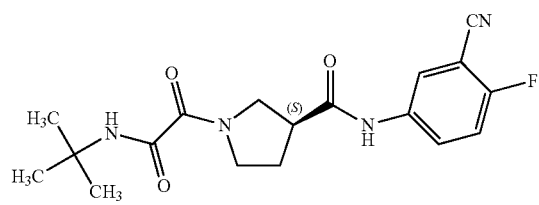

Compound 20 was prepared similarly as described for compound 19, using 5-amino-2-fluorobenzonitrile instead of 3-chloro-2,4-difluoro-aniline in step one. Method D, Rt=1.66 min, m/z=359.1 (M−H)⁻, Exact mass: 360.2. ¹H NMR (400 MHz, DMSO-d₆) δ ppm 1.30 (m, 9H), 1.92-2.29 (m, 2H), 3.06-3.27 (m, 1H), 3.34-4.01 (m, 4H), 7.38-7.58 (m, 1H), 7.77-7.89 (m, 1H), 7.91-8.07 (m, 1H), 8.09-8.19 (m, 1H), 10.32-10.59 (m, 1H) as a mixture of rotamers.

Compound 21: (3S)—N-(3-chloro-2,4-difluoro-phenyl)-1-[2-oxo-2-[[(1R)-2,2,2-trifluoro-1-methyl-ethyl]amino]acetyl]pyrrolidine-3-carboxamide

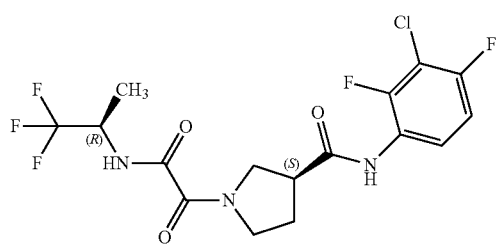

Compound 21 was prepared similarly as described for compound 19, using (R)-1,1,1-trifluoro-2-propylamine instead of tert-butylamine. Method B, Rt=0.97 min, m/z=426.2 (M−H)⁻, Exact mass: 427.1. ¹H NMR (400 MHz, DMSO-d₆) δ ppm 1.27-1.33 (m, 3H), 1.95-2.28 (m, 2H), 3.33-4.00 (m, 5H), 4.52-4.72 (m, 1H), 6.97-7.48 (m, 1H), 7.60-7.91 (m, 1H), 9.01-9.47 (m, 1H), 9.90-10.28 (m, 1H) as a mixture of rotamers.

Compound 22: (3S)—N-(3-cyano-4-fluoro-phenyl)-1-[2-oxo-2-[[(1R)-2,2,2-trifluoro-1-methyl-ethyl]amino]acetyl]pyrrolidine-3-carboxamide

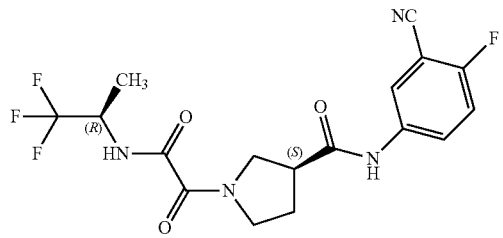

Compound 22 was prepared similarly as described for compound 20, using (R)-1,1,1-trifluoro-2-propylamine instead of tert-butylamine. Method B, Rt=0.87 min, m/z=399.2 (M−H)⁻, Exact mass: 400.1. ¹H NMR (400 MHz, DMSO-d₆) δ ppm 1.30 (d, J=7.0 Hz, 3H), 1.96-2.30 (m, 2H), 3.11-3.28 (m, 1H), 3.38-4.00 (m, 4H), 4.41-4.77 (m, 1H), 7.42-7.56 (m, 1H), 7.78-7.90 (m, 1H), 8.04-8.23 (m, 1H), 9.26 (br. s., 1H), 10.50 (br. s., 1H) as a mixture of rotamers.

Compound 23: (3S)—N-[4-fluoro-3-(trifluoromethyl)phenyl]-1-[2-(isopropylamino)-2-oxo-acetyl]pyrrolidine-3-carboxamide

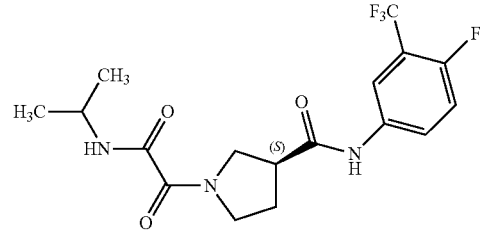

Compound 23 was prepared similarly as described for compound 14, using isopropylamine instead of (R)-1,1,1-trifluoro-2-propylamine. Method B, Rt=0.94 min, m/z=388.2 (M−H)⁻, Exact mass: 389.1. ¹H NMR (400 MHz, DMSO-d₆) δ ppm 1.00-1.17 (m, 6H), 1.94-2.30 (m, 2H), 3.10-3.26 (m, 1H), 3.35-4.02 (m, 5H), 7.36-7.58 (m, 1H), 7.75-7.95 (m, 1H), 8.04-8.19 (m, 1H), 8.36-8.53 (m, 1H), 10.37-10.63 (m, 1H) as a mixture of rotamers.

Compound 24: (3S)—N-[4-fluoro-3-(trifluoromethyl)phenyl]-1-[2-[[(1R)-1-methylpropyl]-amino]-2-oxo-acetyl]pyrrolidine-3-carboxamide

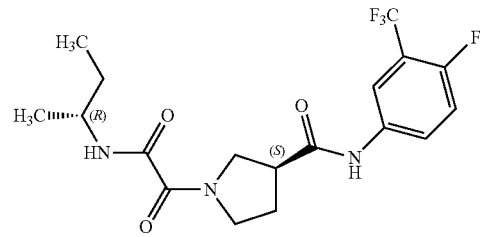

Compound 24 was prepared similarly as described for compound 14, using (R)-(−)-2-aminobutane instead of (R)-1,1,1-trifluoro-2-propylamine. Method B, Rt=0.99 min, m/z=402.2 (M−H)⁻, Exact mass: 403.2. ¹H NMR (400 MHz, DMSO-d₆) δ ppm 0.76-0.88 (m, 3H), 1.00-1.15 (m, 3H), 1.35-1.53 (m, 2H), 1.94-2.29 (m, 2H), 3.11-3.26 (m, 1H), 3.37-4.01 (m, 5H), 7.40-7.53 (m, 1H), 7.79-7.89 (m, 1H), 8.05-8.16 (m, 1H), 8.29-8.46 (m, 1H), 10.35-10.60 (m, 1H) as a mixture of rotamers.

Compound 25: (3S)—N-(3-chloro-4-fluoro-phenyl)-1-[2-oxo-2-[[1-(trifluoromethyl)cyclopropyl]amino]acetyl]pyrrolidine-3-carboxamide

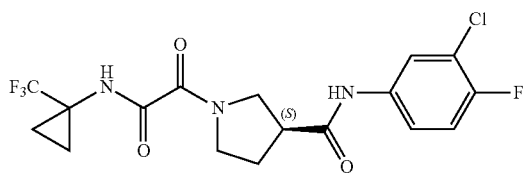

Compound 25 was prepared similarly as described for compound 15, using 1-(trifluoromethyl)cyclopropan-1-amine instead of (R)-1,1,1-trifluoro-2-propylamine.

Method B, Rt=0.97 min, m/z=420.1 (M−H)⁻, Exact mass: 421.1. ¹H NMR (400 MHz, DMSO-d₆) δ ppm 0.95-1.14 (m, 2H), 1.22-1.29 (m, 2H), 1.95-2.29 (m, 2H), 3.09-3.24 (m, 1H), 3.34-3.98 (m, 4H), 7.32-7.41 (m, 1H), 7.42-7.53 (m, 1H), 7.88-7.97 (m, 1H), 9.44 (s, 1H), 10.19-10.35 (m, 1H) as a mixture of rotamers.

Compound 26: (3S)—N-(3-chloro-4-fluoro-phenyl)-1-[2-oxo-2-[[(1S)-2,2,2-trifluoro-1-methyl-ethyl]amino]acetyl]pyrrolidine-3-carboxamide

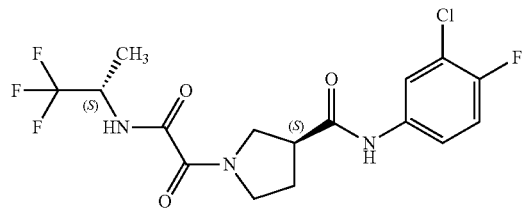

Compound 26 was prepared similarly as described for compound 15, using (S)-1,1,1-trifluoro-2-propylamine instead of (R)-1,1,1-trifluoro-2-propylamine. Method B, Rt=0.97 min, m/z=408.1 (M−H)⁻, Exact mass: 409.1 ¹H NMR (400 MHz, DMSO-d₆) δ ppm 1.26-1.37 (m, 3H), 1.95-2.29 (m, 2H), 3.10-3.27 (m, 1H), 3.34-3.98 (m, 4H), 4.52-4.71 (m, 1H), 7.32-7.41 (m, 1H), 7.43-7.52 (m, 1H), 7.86-7.99 (m, 1H), 9.17-9.33 (m, 1H), 10.22-10.35 (m, 1H) as a mixture of rotamers Compound 27: (2S)—N-(3-cyano-4-fluoro-phenyl)-1-[2-(isopropylamino)-2-oxo-acetyl]-2-methyl-pyrrolidine-3-carboxamide

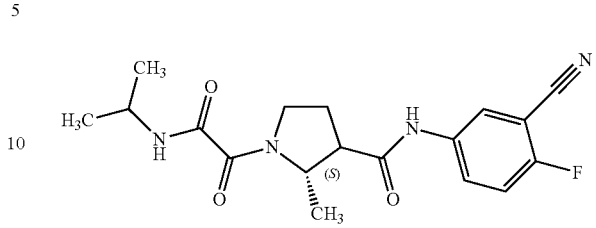

(2S,3S)-methyl 2-methyl-1-((S)-1-phenylethyl)pyrrolidine-3-carboxylate (1.9 g, 7.68 mmol) was dissolved in methanol (50 mL). This was added to Pd/C (10%/0.82 g, 0.77 mmol) under nitrogen. The mixture was stirred under a hydrogen atmosphere at room temperature for 24 hours. The resulting mixture was filtered over a dicalite plug and rinsed using of methanol (100 mL). The filtrate was concentrated in vacuo yielding methyl (2S,3S)-2-methylpyrrolidine-3-carboxylate (830 mg) as a clear oil. Ethyl 2-chloro-2-oxo-acetate (1.3 mL, 11.59 mmol) was added drop wise to a solution of methyl (2S,3S)-2-methylpyrrolidine-3-carboxylate (0.83 g, 5.8 mmol) and diisopropylethylamine (4.99 mL, 28.98 mmol) in dry dichloromethane (5 mL) at room temperature. The reaction mixture was stirred at room temperature for 1 h.

Saturated aqueous NaHCO₃ (5 mL) were added to the reaction mixture and the layers were separated. Then it was extracted using dichloromethane (2×10 mL). The combined extracts were dried on Na₂SO₄, filtered and concentrated in vacuo. The obtained crude was purified by silica gel column chromatography using gradient elution from heptane to EtOAc. (100:0 to 0:100). The desired fractions were concentrated in vacuo yielding methyl (2S,3S)-1-(2-ethoxy-2-oxo-acetyl)-2-methyl-pyrrolidine-3-carboxylate (890 mg) of as a yellow oil.

methyl (2S,3S)-1-(2-ethoxy-2-oxo-acetyl)-2-methyl-pyrrolidine-3-carboxylate (250 mg, 1 mmol) was dissolved in ethanol (10 mL) and isopropylamine (1698 μL, 19.94 mmol) and the mixture was stirred at 60° C. for 2 hours. The mixture was concentrated in vacuo. The obtained oil was purified by silica gel column chromatography using gradient elution from heptane to EtOAc. (100:0 to 0:100). The desired fractions were concentrated under reduced pressure yielding methyl (2S)-1-[2-(isopropylamino)-2-oxo-acetyl]-2-methyl-pyrrolidine-3-carboxylate (380 mg) as a clear oil which was used as such.

Methyl (2S)-1-[2-(isopropylamino)-2-oxo-acetyl]-2-methyl-pyrrolidine-3-carboxylate (0.38 g, 1.48 mmol) was dissolved in tetrahydrofuran (10 mL) and this was stirred at room temperature. To this was added LiOH (178 mg, 7.41 mmol) in water (2 mL) followed by methanol (2 mL). The resulting mixture was stirred at room temperature for 2 hours. Then, HCl (1M in H₂O) (7.41 mL, 1 M, 7.41 mmol) was added and the mixture was concentrated in vacuo until only water remained. Water (5 mL) was added and this solution was extracted using 2-methyl-tetrahydrofuran (3×15 mL). The combined extracts were washed with brine (15 mL), dried on Na₂SO₄, filtered and concentrated in vacuo yielding (2S)-1-[2-(isopropylamino)-2-oxo-acetyl]-2-methyl-pyrrolidine-3-carboxylic acid (312 mg) which was used as such.

(2S)-1-[2-(isopropylamino)-2-oxo-acetyl]-2-methyl-pyrrolidine-3-carboxylic acid (104 mg, 0.43 mmol) was dissolved in N,N-dimethylformamide (1 mL). Then HATU (0.18 g, 0.47 mmol) was added and this mixture was stirred for 20 minutes. Then DIPEA (0.22 mL, 0.75 g/mL, 1.29 mmol) was added followed by 5-amino-2-fluorobenzonitrile (0.12 g, 0.86 mmol). The reaction mixture was stirred at 50° C. for 4 hours. Then this mixture was cooled to room temperature and injected directly onto a silica plug. The mixture was purified by silica gel column chromatography using gradient elution from heptane to EtOAc. (100:0 to 0:100) and further by preperative HPLC (Stationary phase: RP SunFire Prep C18 OBD-10 µm, 30×150 mm, Mobile phase: 0.25% $NH_4HCO_3$ solution in water, MeOH) The desired fractions were concentrated under reduced pressure and co-evaporated twice with methanol (2×15 mL) and dried in a vacuum oven at 55° C. for 18 hours yielding compound 27 (57 mg) as a white powder. Method B, Rt=0.81 (31%) and 0.83 min (69%), m/z=359.2 (M−H)⁻, Exact mass: 360.2

Compound 28: (2S)—N-(3-chloro-2,4-difluoro-phenyl)-1-[2-(isopropylamino)-2-oxo-acetyl]-2-methyl-pyrrolidine-3-carboxamide

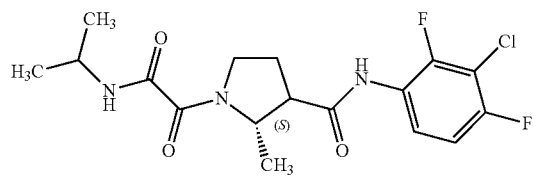

Compound 28 was prepared from (2S)-1-[2-(isopropylamino)-2-oxo-acetyl]-2-methyl-pyrrolidine-3-carboxylic acid similarly as described for compound 27, using 3-chloro-2,4-difluoro-aniline instead of 5-amino-2-fluorobenzonitrile. Method B, Rt=0.91 (48%) and 0.92 min (52%), m/z=386 (M−H)⁻, Exact mass: 387.1.

Compound 29: (2S)—N-(3-chloro-4,5-difluoro-phenyl)-1-[2-(isopropylamino)-2-oxo-acetyl]-2-methyl-pyrrolidine-3-carboxamide

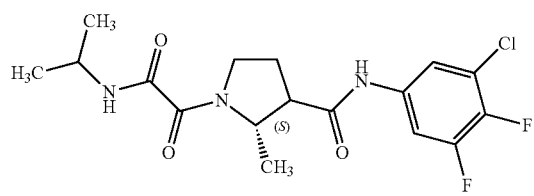

Compound 29 was prepared from (2S)-1-[2-(isopropylamino)-2-oxo-acetyl]-2-methyl-pyrrolidine-3-carboxylic acid similarly as described for compound 27, using 3-chloro-4,5-difluoro-aniline instead of 5-amino-2-fluorobenzonitrile. The diastereomeric mixture 29 (63 mg) was separated via Preperative SFC (Stationary phase: Chiralpak Diacel AD 20×250 mm, Mobile phase: $CO_2$, MeOH with 0.2% iPrNH₂), resulting in 29a (second eluting, 20 mg) and 29b (first eluding, 13.2 mg after further purification by silica gel column chromatography using gradient elution from heptane to iPrOH. (100:0 to 65:35)). 29: Method B, 0.98 (42%) and 1.02 min (58%), m/z=386 (M−H)⁻, Exact mass: 387.1.29a: Method D, Rt=1.89, m/z=386.1 (M−H)⁻, Exact mass: 387.1; ¹H NMR (400 MHz, DMSO-d₆) δ ppm 0.95-1.05 (m, 3H), 1.06-1.16 (m, 6H), 1.82-2.11 (m, 1H), 2.14-2.44 (m, 1H), 3.04-3.26 (m, 1H), 3.35-4.10 (m, 3H), 4.32-4.97 (m, 1H), 7.33-7.85 (m, 2H), 8.20-8.73 (m, 1H), 10.07-10.68 (m, 1H) as a mixture of rotamers. 29b: Method B, Rt=0.97 m/z=386.2 (M−H)⁻, Exact mass: 387.1. ¹H NMR (400 MHz, DMSO-d₆) δ ppm 1.03-1.14 (m, 6H), 1.23-1.31 (m, 3H), 1.93-2.11 (m, 1H), 2.14-2.30 (m, 1H), 2.72-2.93 (m, 1H), 3.30-4.70 (m, 4H), 7.56-7.73 (m, 2H), 8.28-8.54 (m, 1H), 10.22-10.60 (m, 1H) as a mixture of rotamers.

Compound 30: (3S)—N-[3-(difluoromethyl)-4-fluoro-phenyl]-1-[2-oxo-2-[[(1S)-2,2,2-trifluoro-1-methyl-ethyl]amino]acetyl]pyrrolidine-3-carboxamide

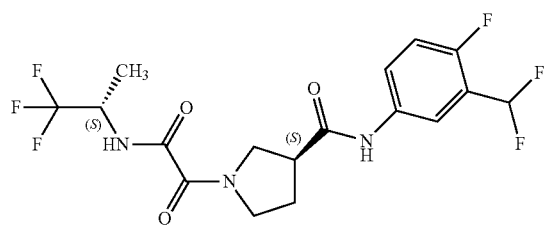

Ethyl 2-[(3S)-3-[[3-(difluoromethyl)-4-fluoro-phenyl]carbamoyl]pyrrolidin-1-yl]-2-oxo-acetate was prepared similarly as described for (9-ethyl 2-(3-((3-bromo-4,5-difluorophenyl)carbamoyl) pyrrolidin-1-yl)-2-oxoacetate using 3-(difluoromethyl)-4-fluoro-aniline instead of 3-bromo-4,5-difluoroaniline. Compound 30 was prepared from ethyl 2-[(3S)-3-[[3-(difluoromethyl)-4-fluoro-phenyl]carbamoyl]pyrrolidin-1-yl]-2-oxo-acetate similar as described for the synthesis of compound 19 from ethyl 2-[(3S)-3-[(3-chloro-2,4-difluoro-phenyl)carbamoyl]pyrrolidin-1-yl]-2-oxo-acetate using (S)-1,1,1-trifluoro-2-propylamine instead of tert-butylamine. Method B, Rt=0.92 min., m/z=424.1 (M−H)⁻, Exact mass: 425.1. ¹H NMR (400 MHz, DMSO-d₆) δ ppm 1.19-1.40 (m, 3H), 1.92-2.30 (m, 2H), 3.08-3.27 (m, 1H), 3.37-4.03 (m, 4H), 4.47-4.78 (m, 1H), 7.20 (m, J=54.4 Hz, 1H), 7.29-7.41 (m, 1H), 7.55-7.80 (m, 1H), 7.86-8.04 (m, 1H), 9.25 (br. s., 1H), 10.30-10.40 (m, 1H) as a mixture of rotamers.

Compound 31: (3S)—N-[3-(difluoromethyl)-4-fluoro-phenyl]-1-[2-(isopropylamino)-2-oxo-acetyl]pyrrolidine-3-carboxamide

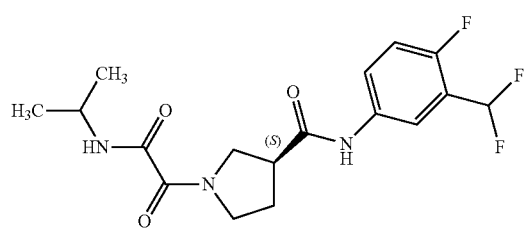

Compound 31 was prepared similarly as described for compound 30, using isopropylamine instead of (S)-1,1,1-trifluoro-2-propylamine. Method B, Rt=0.83 min., m/z=370.2 (M−H)⁻, Exact mass: 371.1. ¹H NMR (400 MHz, DMSO-d$_6$) δ ppm 0.75-1.42 (m, 6H), 1.95-2.29 (m, 2H), 3.05-3.26 (m, 1H), 3.36-4.04 (m, 5H), 7.20 (m, J=54.1, 1H), 7.28-7.37 (m, 1H), 7.63-7.78 (m, 1H), 7.87-8.03 (m, 1H), 8.40-8.50 (m, 1H), 10.25-10.41 (m, 1H) as a mixture of rotamers.

Compound 32: (3S)-1-[2-oxo-2-[[(1R)-2,2,2-trifluoro-1-methyl-ethyl]amino]acetyl]-N-(3,4,5-trifluorophenyl)pyrrolidine-3-carboxamide

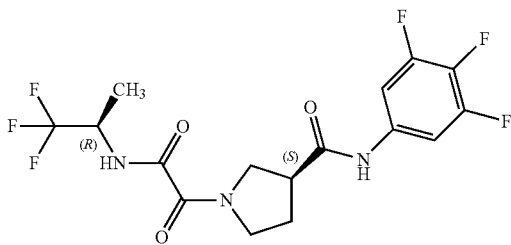

Boc-(3S)-1-pyrrolidine-3-carboxylic acid (1.5 g, 6.97 mmol) and 3,4,5-trifluoroaniline (2.51 g, 17.05 mmol) and HATU (3.18 g, 8.36 mmol) were dissolved in DMF (5 mL). To this was added N,N-diisopropylethylamine (3.6 mL, 0.75 g/mL, 20.91 mmol). The resulting mixture was stirred at room temperature for 2 h. The reaction mixture was loaded on a column and was purified by silica gel column chromatography using gradient elution from heptane to EtOAc. (100:0 to 0:100). The desired fractions were concentrated in vacuo yielding tert-butyl (3S)-3-[(3,4,5-trifluorophenyl)carbamoyl]pyrrolidine-1-carboxylate (2.32 g). Method B, Rt=1.13 min., m/z=343.1 (M−H)⁻, Exact mass: 344.1. HCl (6M in iPrOH, 10 mL, 6 M, 60 mmol) was added to tert-butyl (3S)-3-[(3,4,5-trifluorophenyl)carbamoyl]pyrrolidine-1-carboxylate (2.3 g, 6.35 mmol) in CH$_2$Cl$_2$ (50 mL) and this was stirred at room temperature for 5 days at room temperature. The reaction was concentrated. The residue was taken up in CH$_2$Cl$_2$ (40 mL) and a white precipitate was formed which was collected on a glass filter and dried in a vacuum oven at 55° C. yielding (3S)—N-(3,4,5-trifluorophenyl)pyrrolidine-3-carboxamide hydrochloride (1600 mg) as a bright white powder which was used as such. Method B, Rt=0.69 min., m/z=243.0 (M−H)⁻, Exact mass: 244.1.

Ethyl 2-chloro-2-oxo-acetate (1.98 mL, 1.22 g/mL, 17.69 mmol) was added to a solution of (R)-1,1,1-trifluoro-2-propylamine (2 g, 17.69 mmol) and triethylamine (4.9 mL, 35.37 mmol) in CH$_2$Cl$_2$ (20 mL). The reaction mixture was stirred for 1 hour. NaOH (1M in H$_2$O) (26.5 mL, 1 M, 26.53 mmol) was added and the reaction mixture was stirred vigourously for 2 hours. The organic layer was removed and the aqueous layer was acidified with HCl. The compound was extracted with diethylether (4×25 mL). The combined organic layers were dried over Na$_2$SO$_4$, filtered and evaporated to dryness resulting in 2-oxo-2-[[(1R)-2,2,2-trifluoro-1-methyl-ethyl]amino]acetic acid (2.72 g) as a white powder.

(3S)—N-(3,4,5-trifluorophenyl)pyrrolidine-3-carboxamide hydrochloride (200 mg) and 2-oxo-2-[[(1R)-2,2,2-trifluoro-1-methyl-ethyl]amino]acetic acid (118 mg, 0.64 mmol) were dissolved in DMF (2 mL). HATU (266.74 mg, 0.7 mmol) and DIPEA (0.44 mL, 0.75 g/mL, 2.55 mmol) were added successively. The reaction mixture was stirred at room temperature. The reaction mixture was loaded on a column and purified using silica gel column chromatography (ethyl acetate in heptane from 0 to 100%) to afford compound 32 (83 mg) as a white powder. Method B, Rt=1.04 min., m/z=410.1 (M−H)⁻, Exact mass: 411.1. Differential scanning calorimetry: melting point at 197.3° C. (From 30 to 300° C. at 10° C./min). ¹H NMR (400 MHz, DMSO-d$_6$) δ ppm 1.30 (d, J=7.0 Hz, 3H), 1.92-2.30 (m, 2H), 3.09-3.26 (m, 1H), 3.38-3.99 (m, 4H), 4.50-4.70 (m, 1H), 7.40-7.60 (m, 2H), 9.20-9.31 (m, 1H), 10.42-10.49 (m, 1H) as a mixture of rotamers.

Compound 33: (2S)—N-(3-chloro-4,5-difluorophenyl)-2-methyl-1-[2-oxo-2-[(1R)-(2,2,2-trifluoro-1-methyl-ethyl)amino]acetyl]pyrrolidine-3-carboxamide

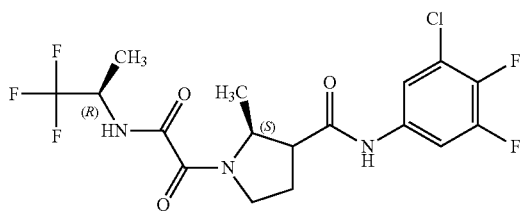

Methyl (2S,3S)-1-(2-ethoxy-2-oxo-acetyl)-2-methyl-pyrrolidine-3-carboxylate (2200 mg, 9.04 mmol) in of methanol (50 mL) was cooled in an ice-water bath. To this was added NaOH (1M in H$_2$O) (9.95 mL, 1 M, 9.95 mmol) drop wise and the mixture was stirred for 30 minutes. The reaction was quenched with HCl (1 M in H$_2$O) (9.5 mL, 1 M, 9.5 mmol) and concentrated to keep 20 mL residue. The residue was extracted with 2-methyl THF (2×20 mL). The combined organic layers were dried (Na$_2$SO$_4$) and evaporated to dryness to afford 2-[(2S,3S)-3-methoxycarbonyl-2-methyl-pyrrolidin-1-yl]-2-oxo-acetic acid (1930 mg) as light yellow solid.

A solution of 2-[(2S,3S)-3-methoxycarbonyl-2-methyl-pyrrolidin-1-yl]-2-oxo-acetic acid (800 mg, 3.64 mmol) in DMF (4 mL, 51.44 mmol) and (R)-1,1,1-trifluoro-2-propylamine (494 mg, 4.37 mmol) was cooled to 0° C. in an ice-water bath. Then HATU (1524 mg, 4.01 mmol) was added while cooling was continued. The reaction mixture was stirred at 0° C. for 30 minutes and allowed to reach room temperature for 1 h. The reaction mixture was loaded on a column and purified using silica gel column chromatography (ethyl acetate in heptane form 0 to 100%) to afford methyl (2S,3S)-2-methyl-1-[2-oxo-2-[[(1R)-2,2,2-trifluoro-1-methyl-ethyl]amino]acetyl]pyrrolidine-3-carboxylate (1000 mg) as colorless oil. Method D, Rt=1.59 min., m/z=309.3 (M−H)⁻, Exact mass: 310.1.

Methyl (2S,3S)-2-methyl-1-[2-oxo-2-[[(1R)-2,2,2-trifluoro-1-methyl-ethyl]amino]acetyl]-pyrrolidine-3-carboxylate (400 mg, 1.29 mmol) was stirred in methanol (10 mL) at room temperature. To this was added NaOH (1M in H$_2$O) (1.35 mL, 1 M, 1.35 mmol) drop wise and the mixture was stirred for 20 hours. After 20 hours more NaOH (1M in H$_2$O) (0.26 mL, 1 M, 0.26 mmol) was added to the reaction mixture which was stirred at room temperature for 2 hours. The reaction was quenched with HCl (1M in H$_2$O) (1.61 mL, 1 M, 1.61 mmol) and concentrated to keep 3 mL residue. The residue was extracted with 2-methyl THF (2×20 mL). The combined organic layers were dried (Na₂SO₄) and evaporated to dryness to afford (2S,3S)-2-methyl-1-[2-oxo-2-[[(1R)-2,2,2-trifluoro-1-methyl-ethyl]amino]acetyl]pyrrolidine-3-carboxylic acid (440 mg) as white solid after standing.

A solution of (2S,3S)-2-methyl-1-[2-oxo-2-[[(1R)-2,2,2-trifluoro-1-methyl-ethyl]amino]-acetyl]pyrrolidine-3-carboxylic acid (190 mg, 0.64 mmol) in DMF (2 mL) and 3-chloro-4,5-difluoroaniline (115.4 mg, 0.71 mmol) was cooled to 0° C. in an ice-water bath. Then HATU (292.6 mg, 0.77 mmol) was added, while cooling was continued. The reaction mixture was stirred at 0° C. for 30 minutes and allowed to reach room temperature for 24 h. The reaction mixture was loaded on a column and purified using silica gel column chromatography (ethyl acetate in heptane form 0 to 100%) and further via preparative HPLC (Stationary phase: RP) (Bridge Prep C18 OBD-10 μm, 30×150 mm, Mobile phase: 0.25% NH₄HCO₃ solution in water, CH₃CN) resulting in compound 33a (40 mg) and compound 33b (33 mg). 33a: (2S,3R)—N-(3-chloro-4,5-difluoro-phenyl)-2-methyl-1-[2-oxo-2-[[(1R)-2,2,2-trifluoro-1-methyl-ethyl]amino]acetyl]pyrrolidine-3-carboxamide Method B, Rt=1.06 min., m/z=440.1 (M−H)⁻, Exact mass: 441.1. 33b: (2S,3S)—N-(3-chloro-4,5-difluoro-phenyl)-2-methyl-1-[2-oxo-2-[[(1R)-2,2,2-trifluoro-1-methyl-ethyl]amino]acetyl]pyrrolidine-3-carboxamide. Method B, Rt=1.11 min., m/z=440.1 (M−H)⁻, Exact mass: 441.1. ¹H NMR (400 MHz, DMSO-d₆) δ ppm 0.99-1.05 (m, 3H), 1.26-1.34 (m, 3H), 1.95-2.06 (m, 1H), 2.23-2.39 (m, 1H), 3.11-3.27 (m, 1H), 3.38-3.84 (m, 2H), 4.46-4.87 (m, 2H), 7.60-7.69 (m, 2H), 9.17-9.43 (m, 1H), 10.24-10.51 (m, 1H) as a mixture of rotamers Compound 34: (2S)-2-methyl-1-[2-oxo-2-[[(1R)-2,2,2-trifluoro-1-methyl-ethyl]amino]acetyl]-N-(3,4,5-trifluorophenyl)pyrrolidine-3-carboxamide

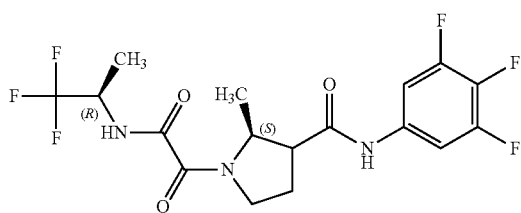

Compound 34a (44 mg) and 34b (52 mg) were prepared similarly as described for compound 33a and 33 b, using 3,4,5-trifluoroaniline instead of 3-chloro-4,5-difluoroaniline. 34a: (2S,3R)-2-methyl-1-[2-oxo-2-[[(1R)-2,2,2-trifluoro-1-methyl-ethyl]amino]acetyl]-N-(3,4,5-trifluorophenyl)pyrrolidine-3-carboxamide Method B, Rt=1.02 min., m/z=424.1 (M−H)⁻, Exact mass: 425.1. 34b: (2S,3S)-2-methyl-1-[2-oxo-2-[[(1R)-2,2,2-trifluoro-1-methyl-ethyl]amino]acetyl]-N-(3,4,5-trifluorophenyl)pyrrolidine-3-carboxamide Method B, Rt=1.05 min., m/z=424.1 (M−H)⁻, Exact mass: 425.1. ¹H NMR (400 MHz, DMSO-d₆) δ ppm 0.99-1.05 (m, 3H), 1.26-1.34 (m, 3H), 1.92-2.07 (m, 1H), 2.19-2.41 (m, 1H), 3.08-3.28 (m, 1H), 3.38-3.85 (m, 2H), 4.45-4.87 (m, 2H), 7.57-7.57 (m, 2H), 9.30 (br. s., 1H), 10.41 (br. s., 1H) as a mixture of rotamers.

Compound 35: N-(3-chloro-2,4-difluoro-phenyl)-2-methyl-1-[2-oxo-2-[((1R)-2,2,2-trifluoro-1-methyl-ethyl)amino]acetyl]piperidine-3-carboxamide

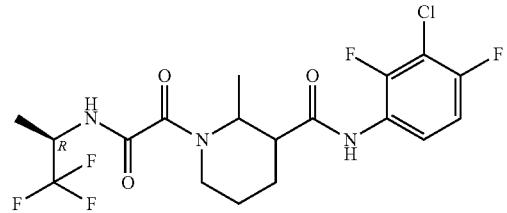

Ethyl 1-(2-ethoxy-2-oxo-acetyl)-2-methyl-piperidine-3-carboxylate was prepared from ethyl 2-methylpiperidine-3-carboxylate, similarly as described for methyl (2S,3S)-1-(2-ethoxy-2-oxo-acetyl)-2-methyl-pyrrolidine-3-carboxylate from methyl (2S,3S)-2-methylpyrrolidine-3-carboxylate. Compound 35 was prepared similarly as described for compound 33, starting from Ethyl 1-(2-ethoxy-2-oxo-acetyl)-2-methyl-piperidine-3-carboxylate instead of methyl (2S,3S)-1-(2-ethoxy-2-oxo-acetyl)-2-methyl-pyrrolidine-3-carboxylate and using 3-chloro-2,4-difluoro-aniline instead of 3-chloro-4,5-difluoroaniline. Compound 35 (550 mg) was separated in diastereoisomers 35a, 35b, 35c and 35d via Preparative SFC (Stationary phase: Chiralpak Daicel IC 20×250 mm, Mobile phase: CO₂, EtOH with 0.2% iPrNH₂). Compound 35a ((2S,3S) or (2R,3R), first eluting on SFC, 70 mg), Method D, Rt=1.86 min., m/z=454.1 (M−H)⁻, Exact mass: 455.1. Compound 35b ((2S,3S) or (2R,3R), second eluting on SFC, 88 mg) Method D, Rt=1.87 min., m/z=454.1 (M−H)⁻, Exact mass: 455.1.

Compound 35c ((2S,3R) or (2R,3S), third eluting on SFC, 86 mg), Method D, Rt=1.89 min., m/z=454.1 (M−H)⁻, Exact mass: 455.1. Compound 35d ((2S,3R) or (2R,3S), fourth eluting on SFC, 106 mg), Method D, Rt=1.88 min., m/z=454.1 (M−H)⁻, Exact mass: 455.1.

Biological Examples

Anti-HBV Activity of Compounds of Formula (I)

The anti-HBV activity was measured using a stable transfected cell line, HepG2.2.15. This cell line was described to secrete relatively consistent high levels of HBV virion particles, which have been shown to cause both acute and chronic infection and disease in chimpanzees.

For the antiviral, assay cells were treated twice for three days with serially diluted compound in 96-well plates in duplicate. After 6 days of treatment the antiviral activity was determined by quantification of purified HBV DNA from secreted virions using realtime PCR and an HBV specific primer set and probe.

The anti HBV activity was also measured using the HepG2.117 cell line, a stable, inducibly HBV producing cell line, which replicates HBV in the absence of doxicycline (Tet-off system). For the antiviral assay, HBV replication was induced, followed by a treatment with serially diluted compound in 96-well plates in duplicate. After 3 days of treatment, the antiviral activity was determined by quantification of intracellular HBV DNA using realtime PCR and an HBV specific primer set and probe.

Cytotoxicity of the compounds was tested using HepG2 cells, incubated for 4 days in the presence of compounds.

The viability of the cells was assessed using a Resazurin assay. Results are displayed in Table 1.

TABLE 1

| Co. No. | HepG2 2.15 EC50 (μM) | HepG2 117 EC50 (μM) | HepG2 4 days CC50 (μM) |
|---|---|---|---|
| 1 | 0.020 | 0.018 | >25 |
| 2 | 0.070 | 0.033 | >25 |
| 3 | 0.141 | 0.026 | >25 |
| 4 | 0.126 | 0.071 | >25 |
| 5 | 0.112 | 0.046 | >25 |
| 6 | 0.301 | 0.257 | >25 |
| 7 | 0.067 | 0.117 | >25 |
| 8 | 0.065 | 0.038 | >25 |
| 9 | 0.120 | 0.134 | >25 |
| 10 | 0.008 | 0.009 | >25 |
| 11 | 0.032 | 0.017 | >25 |
| 12 | 0.321 | 0.115 | >25 |
| 13 | 0.020 | 0.035 | >25 |
| 14 | 0.064 | 0.045 | >25 |
| 15 | 0.025 | 0.047 | >25 |
| 16 | 0.058 | 0.035 | >25 |
| 17a | >1 | >1 | >25 |
| 17b | 0.918 | 0.796 | >25 |
| 17c | >1 | >1 | >25 |
| 17d | 0.070 | 0.032 | >25 |
| 18 |  | 0.670 | >25 |
| 19 | 0.496 | 0.449 | >25 |
| 20 | 0.289 | 0.645 | >25 |
| 21 | 0.063 | 0.063 | >25 |
| 22 | 0.110 | 0.128 | >25 |
| 23 | 0.380 | 0.575 | >25 |
| 24 | 0.134 | 0.384 | >25 |
| 25 | 0.042 | 0.031 | >25 |
| 26 | 0.168 | 0.122 | >25 |
| 27 | 0.119 | 0.126 | >25 |
| 28 | 0.050 | 0.083 | >25 |
| 29a | 0.010 | 0.011 | >25 |
| 29b | >1 | >1 | >25 |
| 29 | 0.018 | 0.048 | >25 |
| 30 | 0.161 | 0.125 | >25 |
| 31 | 0.134 | 0.143 | >25 |
| 32 |  | 0.052 | >25 |
| 33a |  | >0.5 | >25 |
| 33b |  | 0.005 | >25 |
| 34a |  | >0.5 | >25 |
| 34b |  | 0.004 | >25 |
| 35a | >1 | >1 | >25 |
| 35b | 0.195 | 0.483 | >25 |
| 35c | >1 | >1 | >25 |
| 35d | >1 | >1 | >25 |

The invention claimed is:

1. A compound of Formula (I)

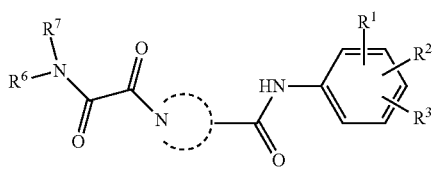

(I)

or a stereoisomer or tautomeric form thereof, wherein:

is

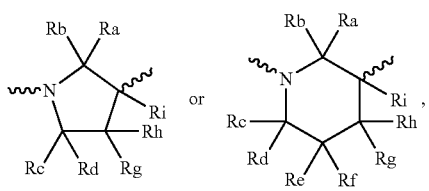

each of Ra, Rb, Rc, Rd, Re, Rf and Rg are independently selected from the group consisting of hydrogen and methyl;
Rh is hydrogen;
Ri is hydrogen;
$R^1$, $R^2$ and $R^3$ are independently selected from the group consisting of hydrogen, fluoro, chloro, bromo, —$CHF_2$, —$CH_2F$, —$CF_3$, —CN and methyl;
$R^6$ is selected from the group consisting of $C_1$-$C_6$alkyl and a 3-7 membered saturated ring optionally containing one or more heteroatoms each independently selected from the group consisting of O, S and N, said $C_1$-$C_6$alkyl and 3-7 membered saturated ring each optionally substituted with one or more substituents selected from the group consisting of fluoro and $C_1$-$C_3$alkyl, wherein said $C_1$-$C_3$alkyl is optionally substituted with one or more substituents selected from the group consisting of fluoro, —CN, and OH;
$R^7$ is hydrogen;
or a pharmaceutically acceptable salt or a solvate thereof.

2. A compound of Formula (II) according to claim 1

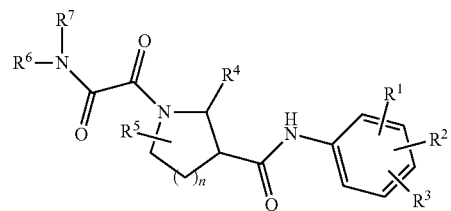

(II)

or a stereoisomer or tautomeric form thereof, wherein:
n is 1 or 2;
$R^1$, $R^2$ and $R^3$ are independently selected from the group consisting of hydrogen, fluoro, chloro, bromo, —$CHF_2$, —$CH_2F$, —$CF_3$, —CN and methyl;
$R^4$ and $R^5$ are independently selected from hydrogen or methyl;
$R^6$ is selected from the group consisting of $C_1$-$C_6$alkyl and a 3-7 membered saturated ring optionally containing one or more heteroatoms each independently selected from the group consisting of O, S and N, said $C_1$-$C_6$alkyl and 3-7 membered saturated ring each optionally substituted with one or more substituents selected from the group consisting of fluoro and $C_1$-$C_3$alkyl wherein said $C_1$-$C_3$alkyl is optionally substituted with one or more substituents selected from the group consisting of fluoro, —CN, and OH;
$R^7$ is hydrogen;
or a pharmaceutically acceptable salt or a solvate thereof.

3. A compound according to claim 1, wherein $R^1$ is selected from the group consisting of hydrogen, fluoro, chloro, —$CHF_2$, —CN, —$CF_3$ and methyl.

4. A compound according to claim 1, wherein at least two of $R^1$, $R^2$ and $R^3$ are each independently fluoro, chloro or bromo.

5. A compound according to claim 2, wherein $R^4$ is methyl.

6. A compound according to claim 1, wherein $R^6$ is a 3-7 membered saturated ring optionally containing one oxygen, wherein said 3-7 membered saturated ring is optionally substituted with methyl.

7. A compound according to claim 1, wherein $R^6$ is a 4 or 5 membered saturated ring containing one oxygen, wherein said 4 or 5 membered saturated ring is optionally substituted with methyl.

8. A compound according to claim 1, wherein $R^6$ is a branched $C_1$-$C_6$alkyl optionally substituted with one or more fluoro.

9. A compound of Formula (III) according to claim 2

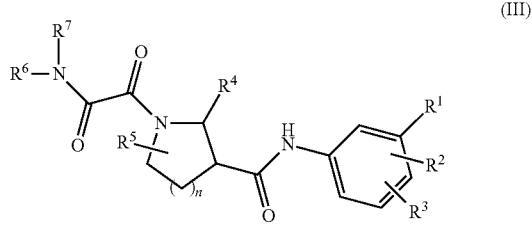

wherein $R^1$ is not hydrogen.

10. A compound according to claim 1, wherein the stereochemical configuration of atom (*) is as follows

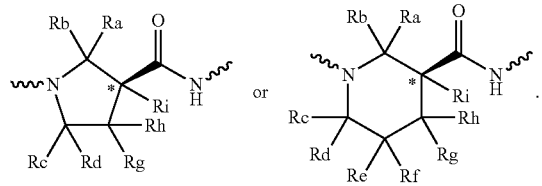

11. A pharmaceutical composition comprising a compound according to claim 1, and a pharmaceutically acceptable carrier.

12. A compound according to claim 1 in combination with at least one other anti-HBV agent.

13. A compound according to claim 2, wherein $R^1$ is selected from the group consisting of hydrogen, fluoro, chloro, —$CHF_2$, —CN, —$CF_3$ and methyl.

14. A compound selected from the group consisting of:
(S)—N-(3-bromo-4,5-difluorophenyl)-1-(2-oxo-2-(((R)-1,1,1-trifluoropropan-2-yl)amino)acetyl)pyrrolidine-3-carboxamide;
(S)—N-(3-bromo-4,5-difluorophenyl)-1-(2-((3-methyloxetan-3-yl)amino)-2-oxoacetyl)pyrrolidine-3-carboxamide;
(S)—N-(3-bromo-4,5-difluorophenyl)-1-(2-(tert-butylamino)-2-oxoacetyl)pyrrolidine-3-carboxamide;
(3S)—N-(4-Fluoro-3-methylphenyl)-1-{[(1-methylethy) amino](oxo)acetyl}pyrrolidine-3-carboxamide;
(S)-1-(2-(cyclopentylamino)-2-oxoacetyl-N-(4-fluoro-3-methylphenyl)pyrrolidine-3-carboxamide;
(S)—N-(4-fluoro-3-methylphenyl)-1-(2-(((R)-1-hydroxypropan-2-yl)amino)-2-oxoacetyl)pyrrolidine-3-carboxamide;
(3S)—N-(4-Fluoro-3-methylphenyl)-1-{[(3-methyloxetan-3-yl)amino](oxo)acetyl}pyrrolidine-3-carboxamide;
(3S)—N-(4-Fluoro-3-methylphenyl)-1-[{[(1R)-1-methylpropyl]amino}(oxo)acetyl]pyrrolidine-3-carboxamide;
(3S)—N-(4-Fluoro-3-methylphenyl)-1-{oxo[(3S)-tetrahydrofuran-3-ylamino]acetyl}pyrrolidine-3-carboxamide;
(2S, 3S)—N-(4-Fluoro-3-methylphenyl)-2-methyl-1-{[(3-methyloxetan-3-yl)-amino](oxo) acetyl}pyrrolidine-3-carboxamide;
(S)—N-(3-chloro-4,5-difluorophenyl)-1-(2-oxo-2-(((R)-1,1,1-trifluoropropan-2-yl)amino)acetyl)pyrrolidine-3-carboxamide;
(3S)—N-(4-Fluoro-3-methylphenyl)-1-{[(1-methylethyl)amino](oxo)acetyl}piperidine-3-carboxamide;
(S)—N-(3-chloro-4,5-difluorophenyl)-1-(2-oxo-2-((1-(trifluoromethyl) cyclopropyl)amino)acetyl)pyrrolidine-3-carboxamide;
(S)—N-(4-fluoro-3-(trifluoromethyl)phenyl)-1-(2-oxo-2-(((R)-1,1,1-trifluoropropan-2-yl)amino)acetyl)pyrrolidine-3-carboxamide;
(S)—N-(3-chloro-4,5-difluorophenyl)-1-(2-oxo-2-((1,1,1-trifluoro-2-methylpropan-2-yl)amino)acetyl)pyrrolidine-3-carboxamide;
N-(4-fluoro-3-methylphenyl)-5-methyl-1-(2-((3-methyloxetan-3-yl)amino)-2-oxoacetyl)pyrrolidine-3-carboxamide;
N-(3-chloro-4,5-difluoro-phenyl)-2,2-dimethyl-1-[2-oxo-2-[[(1R)-2,2,2-trifluoro-1-methyl-ethyl]amino]acetyl]pyrrolidine-3-carboxamide;
(3S)-1-[2-(tert-butylamino)-2-oxo-acetyl]-N-(3-chloro-2,4-difluoro-phenyl)pyrrolidine-3-carboxamide;
(3S)-1-[2-(tert-butylamino)-2-oxo-acetyl]-N-(3-cyano-4-fluorophenyl)pyrrolidine-3-carboxamide;
(3S)—N-(3-chloro-2,4-difluoro-phenyl)-1-[2-oxo-2-[[(1R)-2,2,2-trifluoro-1-methyl-ethyl]amino]acetyl] pyrrolidine-3-carboxamide;
(3S)—N-(3-cyano-4-fluoro-phenyl)-1-[2-oxo-2-[[(1R)-2,2,2-trifluoro-1-methyl-ethyl]amino]acetyl]pyrrolidine-3-carboxamide;
(3S)—N-[4-fluoro-3-(trifluoromethyl)phenyl]-1-[2-(isopropylamino)-2-oxo-acetyl]pyrrolidine-3-carboxamide;
(3S)—N-[4-fluoro-3-(trifluoromethyl)phenyl]-1-[2-[[(1R)-1-methylpropyl]amino]-2-oxo-acetyl]pyrrolidine-3-carboxamide;
(3S)—N-(3-chloro-4-fluoro-phenyl)-1-[2-oxo-2-[[1-(trifluoromethyl)cyclopropyl]amino]acetyl]pyrrolidine-3-carboxamide;
(3S)—N-(3-chloro-4-fluoro-phenyl)-1-[2-oxo-2-[[(1S)-2,2,2-trifluoro-1-methyl-ethyl]amino]acetyl]pyrrolidine-3-carboxamide;
(2S)—N-(3-cyano-4-fluoro-phenyl)-1-[2-(isopropylamino)-2-oxo-acetyl]-2-methyl-pyrrolidine-3-carboxamide;
(2S)—N-(3-chloro-2,4-difluoro-phenyl)-1-[2-(isopropylamino)-2-oxo-acetyl]-2-methyl-pyrrolidine-3-carboxamide;
(2S)—N-(3-chloro-4,5-difluoro-phenyl)-1-[2-(isopropylamino)-2-oxo-acetyl]-2-methyl-pyrrolidine-3-carboxamide;
(3S)—N-[3-(difluoromethyl)-4-fluoro-phenyl]-1-[2-oxo-2-[[(1S)-2,2,2-trifluoro-1-methyl-ethyl]amino]acetyl]pyrrolidine-3-carboxamide;
(3S)—N-[3-(difluoromethyl)-4-fluoro-phenyl]-1-[2-(isopropylamino)-2-oxo-acetyl]pyrrolidine-3-carboxamide;

(3S)-1-[2-oxo-2-[[(1R)-2,2,2-trifluoro-1-methyl-ethyl]amino]acetyl]-N-(3,4,5-trifluorophenyl)pyrrolidine-3-carboxamide;

(2S)—N-(3-chloro-4,5-difluoro-phenyl)-2-methyl-1-[2-oxo-2-[(1R)-(2,2,2-trifluoro-1-methyl-ethyl)amino]acetyl]pyrrolidine-3-carboxamide;

(2S)-2-methyl-1-[2-oxo-2-[[(1R)-2,2,2-trifluoro-1-methyl-ethyl]amino]acetyl]-N-(3,4,5-trifluorophenyl)pyrrolidine-3-carboxamide; and N-(3-chloro-2,4-difluoro-phenyl)-2-methyl-1-[2-oxo-2-[((1R)-2,2,2-trifluoro-1-methyl-ethyl)amino]acetyl]piperidine-3-carboxamide.

15. A pharmaceutical composition comprising a compound according to claim 14, and a pharmaceutically acceptable carrier.

16. A method of treating an HBV infection in a subject comprising administering to said subject a therapeutically effective amount of at least one compound of claim 1, and optionally an additional anti-HBV agent.

17. A method of treating an HBV infection in a subject comprising administering to said subject a therapeutically effective amount of at least one compound of claim 14, and optionally an additional anti-HBV agent.

18. A compound according to claim 1 in combination with at least one other anti-HBV agent, wherein the at least one other anti-HBV agent is selected from the group consisting of interferon, pegylated interferon, 3TC, adefovir and Toll-like receptor 7 and/or 8 agonists or combinations thereof.

19. A pharmaceutical composition comprising a compound according to claim 1, a pharmaceutically acceptable carrier and optionally at least one other anti-HBV agent.

* * * * *